United States Patent
Edwards et al.

(10) Patent No.: US 8,313,484 B2
(45) Date of Patent: *Nov. 20, 2012

(54) GERD TREATMENT APPARATUS AND METHOD

(75) Inventors: Stuart D Edwards, Salinas, CA (US);
David S Utley, Redwood City, CA (US)

(73) Assignee: Mederi Therapeutics Inc., Greenwich, CT (US)

( * ) Notice: Subject to any disclaimer, the term of this patent is extended or adjusted under 35 U.S.C. 154(b) by 627 days.

This patent is subject to a terminal disclaimer.

(21) Appl. No.: 11/254,951

(22) Filed: Oct. 20, 2005

(65) Prior Publication Data

US 2006/0041256 A1 Feb. 23, 2006

Related U.S. Application Data

(60) Division of application No. 10/428,458, filed on May 2, 2003, now Pat. No. 6,971,395, which is a division of application No. 10/084,590, filed on Feb. 27, 2002, now Pat. No. 6,589,238, which is a continuation of application No. 09/007,283, filed on Jan. 14, 1998, now abandoned.

(51) Int. Cl.
*A61B 18/14* (2006.01)
*A61B 19/00* (2006.01)

(52) U.S. Cl. .......................... 606/41; 128/898; 607/133

(58) Field of Classification Search .................. 606/41, 606/48–50; 607/101–105, 133; 128/898
See application file for complete search history.

(56) References Cited

U.S. PATENT DOCUMENTS

| | | | |
|---|---|---|---|
| 1,798,902 A | 3/1931 | Raney | |
| 3,517,128 A | 6/1970 | Hines | |
| 3,901,241 A | 8/1975 | Allen, Jr. | |
| 4,011,872 A | 3/1977 | Komiya | |
| 4,196,724 A | 4/1980 | Wirt et al. | |
| 4,411,266 A | 10/1983 | Cosman | |
| 4,423,812 A | 1/1984 | Sato | |
| 4,532,924 A | 8/1985 | Auth et al. | |
| 4,565,200 A | 1/1986 | Cosman | |
| 4,705,041 A | 11/1987 | Kim | |
| 4,901,737 A | 2/1990 | Toone | |
| 4,906,203 A | 3/1990 | Margrave et al. | |
| 4,907,589 A | 3/1990 | Cosman | |
| 4,943,290 A | 7/1990 | Rexroth et al. | |

(Continued)

FOREIGN PATENT DOCUMENTS

DE          43 03 882          2/1995

(Continued)

OTHER PUBLICATIONS

Dallemagne, B. et al., "Laparoscopic Nissen Fundoplication: Preliminary." Surgical Laparoscopy & Endoscopy. 1991 1(3): 138-43.

Mugica et al. Direct Diaphragm Stimulation, Jan. 1987 PACE, vol. 10, pp. 252-256.

Mugica et al., Neurostimulation: An Overview, Chapter 21, Preliminary Test of a Muscular Diaphragm pacing System on Human Patients. 1985. pp. 3. 263-279.

Rice et al., Endoscopic Paranasal Sinus Surgery, Chapter 5, Functional Endoscopic Paranasal Sinus Surgery, The Technique of Messerklinger, Raven Press, 1988, pp. 75-104.

Rice et al., Endoscopic Paranasal Sinus Surgery, Chapter 6, Total Endoscopic Sphenoethmoidectomy, The Technique of Wigand, Raven Press, 1988, pp. 105-125.

* cited by examiner

*Primary Examiner* — Michael Peffley

(57) ABSTRACT

A method of forming a composite lesion pattern in a tissue region at or near a sphincter comprising providing a catheter having a plurality of energy delivery devices coupled to the catheter. The catheter is introduced at least partially into the sphincter. Energy is delivered from the energy delivery devices to produce the composite lesion pattern. The composite lesion pattern comprises a radial distribution of lesions about the tissue region and a longitudinal distribution of lesions along the tissue region.

7 Claims, 29 Drawing Sheets

U.S. PATENT DOCUMENTS

| | | |
|---|---|---|
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,236,413 A | 8/1993 | Feiring |
| 5,242,441 A | 9/1993 | Avitall |
| 5,254,126 A | 10/1993 | Filipi et al. |
| 5,256,138 A | 10/1993 | Burek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,304,214 A | 4/1994 | DeFord et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,415,657 A | 5/1995 | Taymor-Luia |
| 5,421,819 A | 6/1995 | Edwards et al. |
| 5,423,808 A | 6/1995 | Edwards et al. |
| 5,423,811 A | 6/1995 | Imran et al. |
| 5,423,812 A | 6/1995 | Ellman et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A * | 5/1996 | Imran ............................ 606/41 |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,609,151 A | 3/1997 | Mulier et al. |
| 5,624,439 A | 4/1997 | Edwards et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,738,096 A | 4/1998 | Ben-Haim |
| 5,830,213 A | 11/1998 | Panescu et al. |
| 5,836,874 A | 11/1998 | Swanson et al. |
| 5,860,974 A | 1/1999 | Abele |
| 5,871,483 A | 2/1999 | Jackson et al. |
| 5,957,920 A * | 9/1999 | Baker ............................ 606/33 |
| 6,073,052 A * | 6/2000 | Zelickson et al. ............ 607/100 |
| 6,102,929 A | 8/2000 | Conway et al. |
| 6,156,032 A * | 12/2000 | Lennox ........................... 606/41 |
| 6,363,937 B1 * | 4/2002 | Hovda et al. ................. 128/898 |
| 7,462,179 B2 | 12/2008 | Edwards et al. |

FOREIGN PATENT DOCUMENTS

| | | |
|---|---|---|
| DE | 38 38 840 | 2/1997 |
| EP | 0 139 607 | 5/1985 |
| EP | 0 608 609 | 8/1994 |

OTHER PUBLICATIONS

Hinder, R.A. et al., "The Technique of Laparoscopic Nissen Fundoplication." Surgical Laparoscopy & Endoscopy. 1992. 2(3): 265-272.

Karlstrom, L.H. et al. "Ectopic jejunal pacemakers and enterogastric reflux after Roux gastrectomy: Effect of intestinal pacing." Surgery 1989. 106(3): 486-495.

Kelly, K.A. et al., "Doudenal-gastric reflux and slowed gastric emptying by electrical pacing of the canine duodenal pacesetter potential." Gastroenterology. 1977. 72(3): 429-33.

Urschel, J.D. "Complications of Antireflux Surgery." Am J Surg. 1993. 166(1): 68-70.

Kaneko, et al., Physiological Laryngeal Pacemaker, May 1985, Trans Am Soc. Artif. Intern Organs, vol. XXXI, pp. 293-296.

GERD TREATMENT APPARATUS AND METHOD

RELATED APPLICATIONS

This application is a divisional of U.S. patent application Ser. No. 10/428,458, filed May 2, 2003, now U.S. Pat. No. 6,971,395, which is a divisional of U.S. patent application Ser. No. 10/084,590, filed Feb. 27, 2002, now U.S. Pat. No. 6,589,238, and entitled "Sphincter Treatment Device," which is a continuation of U.S. patent application Ser. No. 09/007,238, filed Jan. 14, 1998, now abandoned.

FIELD OF THE INVENTION

This invention relates generally to an apparatus and method for the treatment of sphincters, and more specifically to an apparatus and method that treat esophageal sphincters.

BACKGROUND OF THE INVENTION

Gastroesophageal reflux disease (GERD) is a common gastroesophageal disorder in which the stomach contents are ejected into the lower esophagus due to a dysfunction of the lower esophageal sphincter (LES). These contents are highly acidic and potentially injurious to the esophagus resulting in a number of possible complications of varying medical severity. The reported incidence of GERD in the U.S. is as high as 10% of the population (Castell D O; Johnston B T: Gastroesophageal Reflux Disease: Current Strategies For Patient Management. Arch Fam Med, 5(4):221-7; (1996 April)).

Acute symptoms of GERD include heartburn, pulmonary disorders and chest pain. On a chronic basis, GERD subjects the esophagus to ulcer formation, or esophagitis and may result in more severe complications including esophageal obstruction, significant blood loss and perforation of the esophagus. Severe esophageal ulcerations occur in 20-30% of patients over age 65. Moreover, GERD causes adenocarcinoma, or cancer of the esophagus, which is increasing in incidence faster than any other cancer (Reynolds J C: Influence Of Pathophysiology, Severity, And Cost On The Medical Management Of Gastroesophageal Reflux Disease. Am J Health Syst Pharm, 53(22 Supp13):S5-12 (1996 Nov. 15)).

Current drug therapy for GERD includes histamine receptor blockers which reduce stomach acid secretion and other drugs which may completely block stomach acid. However, while pharmacologic agents may provide short term relief, they do not address the underlying cause of LES dysfunction.

Invasive procedures requiring percutaneous introduction of instrumentation into the abdomen exist for the surgical correction of GERD. One such procedure, Nissen fundoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. In fact, a recent 10 year, 344 patient study reported the morbidity rate for this procedure to be 17% and mortality 1% (Urschel, J D: Complications Of Antireflux Surgery, Am J Surg 166(1): 68-70; (1993 July)). This rate of complication drives up both medical cost and convalescence period for the procedure and may exclude portions of certain patient populations (e.g., the elderly and immuno-compromised).

Efforts to perform Nissen fundoplication by less invasive techniques have resulted in the development of laparoscopic Nissen fundoplication. Laparoscopic Nissen fundoplication, reported by Dallemagne et al. Surgical Laparoscopy and Endoscopy, Vol. 1, No. 3, (1991), pp. 138-43 and by Hindler et al. Surgical Laparoscopy and Endoscopy, Vol. 2, No. 3, (1992), pp. 265-272, involves essentially the same steps as Nissen fundoplication with the exception that surgical manipulation is performed through a plurality of surgical cannula introduced using trocars inserted at various positions in the abdomen.

Another attempt to perform fundoplication by a less invasive technique is reported in U.S. Pat. No. 5,088,979. In this procedure, an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Yet another attempt to perform fundoplication by a less invasive technique is reported in U.S. Pat. No. 5,676,674. In this procedure, invagination is done by a jaw-like device and fastening of the invaginated gastroesophageal junction to the fundus of the stomach is done via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to LES and the risk of leaks developing at the newly created gastroesophageal junction.

There is a need in the art for a less invasive GERD treatment apparatus that does not require major surgical intervention or require the introduction of foreign materials into the body. Yet another need exists for a method of treating GERD that does not involve the medical risks of leakage and infection developing at an artificially created gastroesophageal junction. Yet another need exists for an apparatus that treats GERD with minimum trauma to the LES.

SUMMARY OF THE INVENTION

Accordingly, an object of the invention is to provide an apparatus and method for the treatment of GERD.

Another object of the invention is to provide an apparatus and method to treat GERD using minimally invasive surgical methods such as non-percutaneously.

Yet another object of the invention is to provide an apparatus and method to treat the esophageal sphincters using minimally invasive surgical methods.

Another object of the invention is to provide an apparatus and method to tighten the LES.

A further other object of the invention is to provide an apparatus and method to reduce the frequency of spontaneous relaxation and opening of the LES.

Yet another object of the invention is to provide an apparatus and methods to reduce the frequency and severity of gastroesophageal reflux events.

These and other objects of the invention are provided in an apparatus that includes a first expandable member that is expandable by an expansion medium. The first expandable member includes an exterior and a plurality of apertures. The expansion medium is released from the first expandable member when a sufficient pressure is applied to the expansion medium housed in an interior of the first expandable member. A second expandable member is positioned at least partially adjacent to the first expandable member. The second expandable member is configured to receive at least a portion of the expansion medium from the interior of the first expandable member. An electromagnetic energy delivery device is coupled to one of the first or second expandable members and is configured to be coupled to a power source. The first and second expandable members are sized to be expanded sufficiently to open a sphincter.

These and other objects of the invention are provided in a method of forming a composite lesion pattern in a tissue region at or near a sphincter. The method provides a catheter having a plurality of energy delivery devices coupled to the catheter. The catheter is introduced at least partially into the sphincter. Energy is delivered from the energy delivery devices to produce the composite lesion pattern. The composite lesion pattern comprises a radial distribution of lesions about the tissue region and a longitudinal distribution of lesions along the tissue region. According to one aspect of the invention, the method comprises the further step of introducing a cooling fluid to cool at least a portion of the tissue region. According to another aspect of the invention, the method comprises the further step of introducing a cooling fluid to cool at least a portion of at least one energy delivery device.

In one embodiment, the pattern is a concentric circle of lesions all at a fixed depth along the radial axis of the sphincter.

In another embodiment, the pattern is a wavy or folded circle of lesions at varying depths along the radial axis of the sphincter.

In yet another embodiment, the pattern is a random distribution of lesions at varying depths and evenly spaced in a radial direction.

In still another embodiment, the pattern is an eccentric pattern of lesions in one or more radial locations.

DETAILED DESCRIPTION

Figure 1:
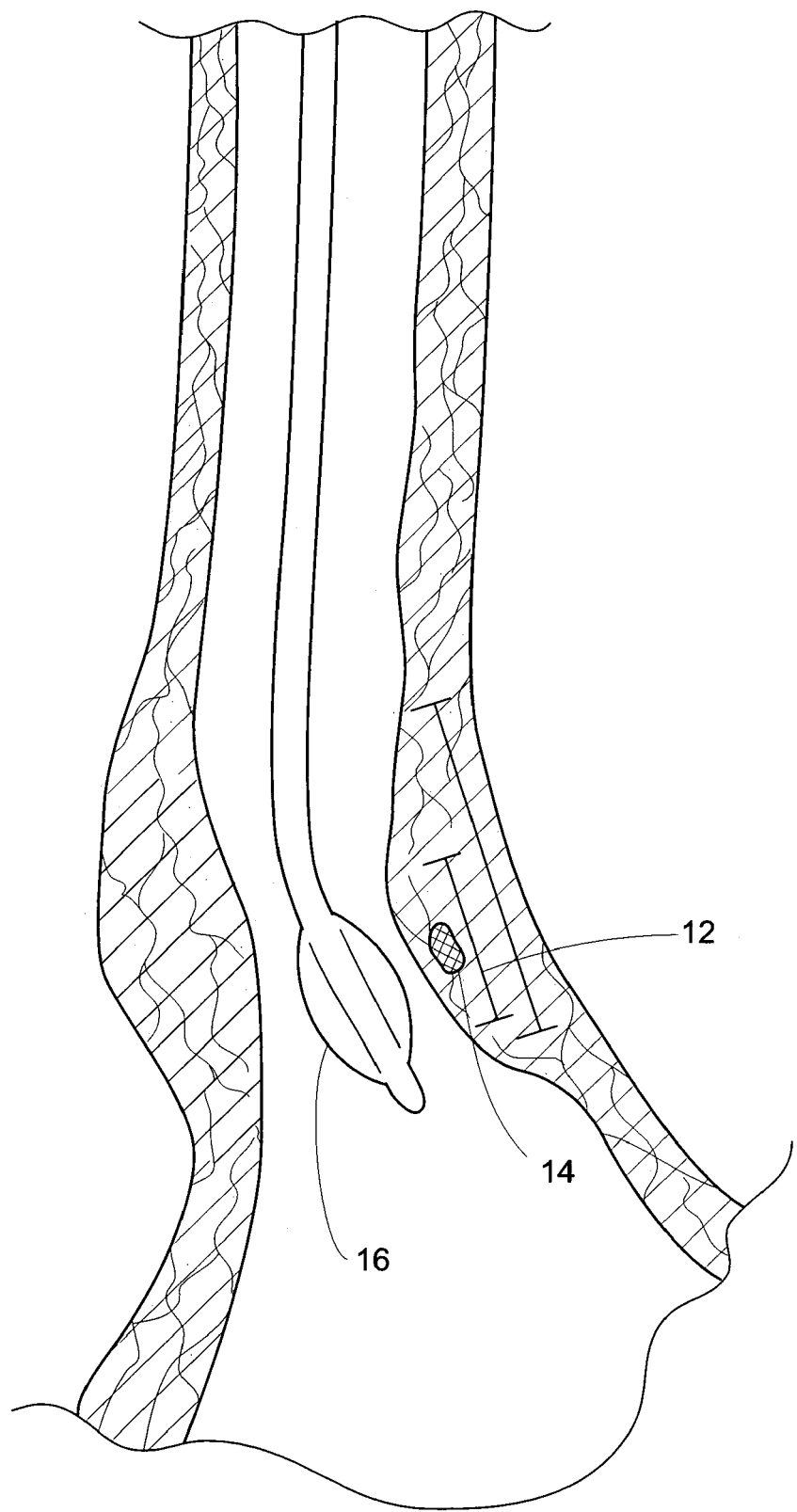
FIG. 1 is an illustrated lateral view of the upper GI tract including the esophagus and lower esophageal sphincter and the positioning of the GERD treatment apparatus of the present invention the lower esophageal sphincter.
Figure 2:
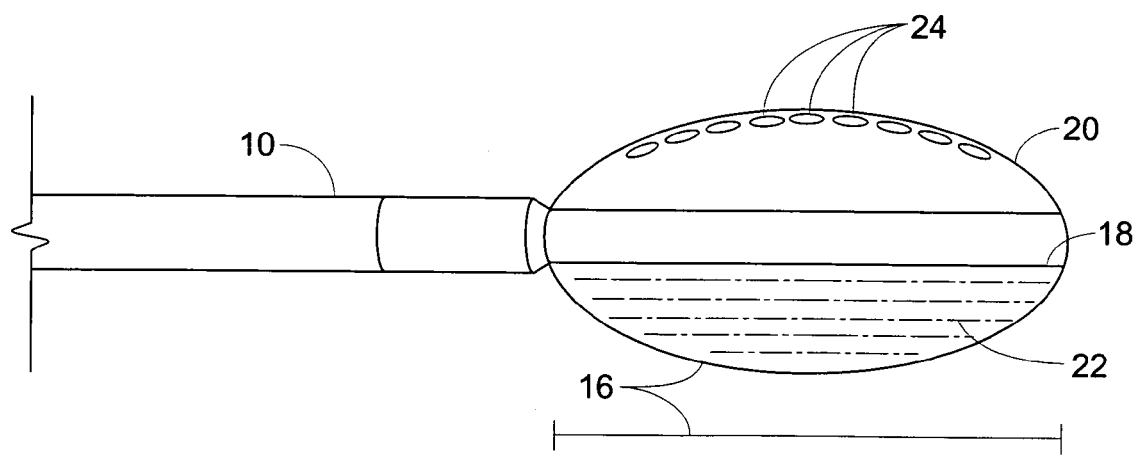
FIG. 2 is a lateral view of the present illustrating apertures in the expandable member.

Referring now to FIGS. 1 and 2, one embodiment of GERD treatment apparatus 10 that is used to deliver energy to a treatment site 12 to produce lesions 14 in the LES includes a first expandable member 16 with an interior surface 18 and an exterior surface 20. First expandable member 16, which can also be an energy delivery device support member, is configured to receive an expansion medium 22 that inflates first expandable member 16 from a compacted, non-deployed state to a deployed state. Exterior surface 20 includes a plurality of apertures 24. Upon the application of sufficient pressure, first expandable member 16 weeps expansion medium 22 from interior surface 18.

While expandable member 16, with a single interior surface 18, is preferred, it will be appreciated that expandable member 16 can be made of different compositions or materials, with one or more open or closed cells or chambers. The plurality of such cells or chambers can be compressed or configured in a small diameter for insertion, and are then expanded after insertion to establish the desired electrical contact with the targeted surface of the esophagus.

Expansion medium 22 may be a gas, fluid or the like. In various embodiments, the expansion medium 22 can be an electrolytic solution. In other embodiments, expansion medium 22 can also be a contrast solution to facilitate imaging of the procedure by fluoroscopy or ultrasonography. Yet in other embodiments, GERD treatment apparatus 10 can include visualization capability including, but not limited to a viewing scope, ultrasound, an expanded eyepiece, fiber optics (including illumination and imaging fibers), video imaging, a light source and the like.

Figure 3:
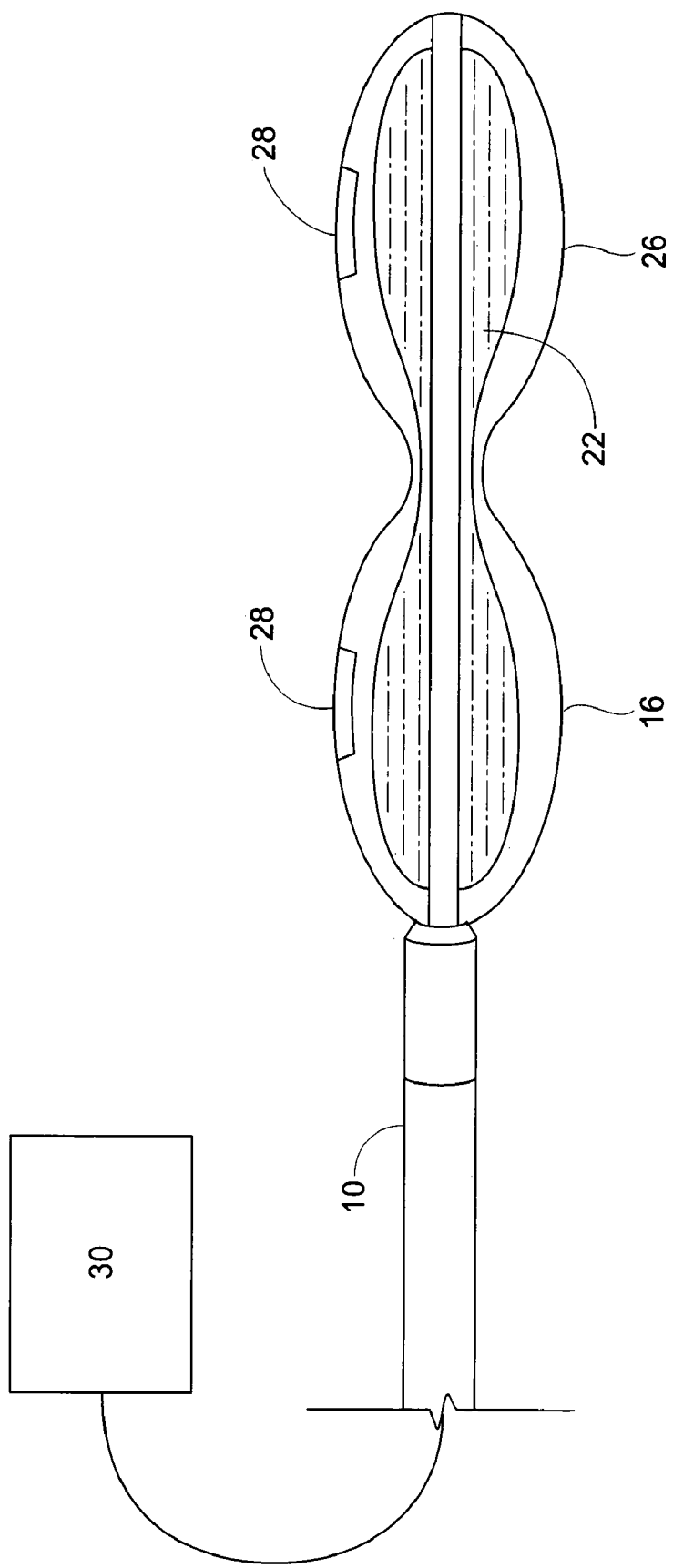
FIG. 3 illustrates a lateral view of an embodiment of the invention that includes two expandable members and an electrode coupled to a power source.

Referring to FIG. 3, a second expandable member 26 can be positioned at least partially adjacent to first expandable member 16. Second expandable member 26 receives at least a portion of the expansion medium 22 from interior surface 18.

An electromagnetic energy delivery device 28 is coupled to one of the first or second expandable members 16 and 26, respectively, and configured to be coupled to a power source 30.

First and second expandable members 16 and 26 are sized to be expanded to sufficiently dilate the esophagus such that all or a portion of the interior of the lower esophageal sphincter can be accessible to the energy delivery device 28. Expandable members 16 or 26 can dilate the esophageal sphincter in a range of 5-40 mms. It will be appreciated that other devices capable of being in confined non-deployed states, during their introduction into the esophagus and thereafter expanded to deployed states at or near the LES, can be utilized. Such devices include, but are not limited to, basket-shaped devices made of superelastic metals such as nitinol.

Figure 4:
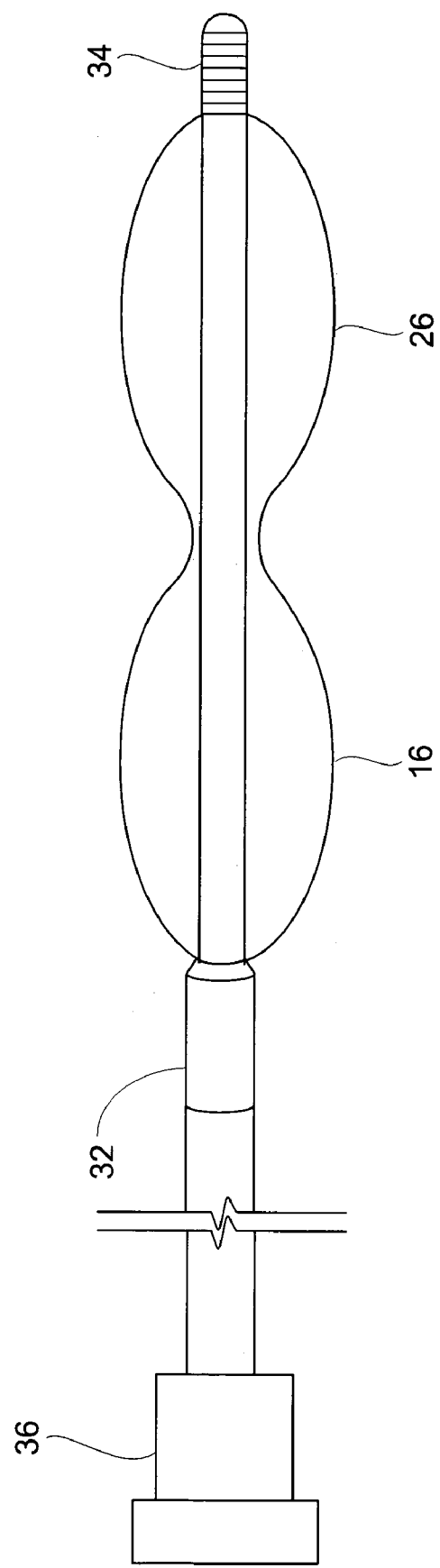
FIG. 4 illustrates a lateral view of a proximal fitting and distal segments of an embodiment of the invention.

Referring to FIG. 4, an extension member 32 with a distal segment 34 is configured to be coupled to first and/or second expandable members 16 and 26. In one embodiment, extension member 32 is rod-like and can be malleable, flexible, articulated and steerable. In various embodiments, extension member 32 can contain optics, fluid and gas paths, sensor and electronic cabling. In one embodiment, extension member 32 can be a coil-reinforced multilumen catheter, as is well known to those skilled in the art. Extension member 32 has sufficient length to position the first and second expandable members in the LES and/or stomach using a trans-oral approach. Typical lengths include, but are not limited to, a range of 40-180 cms. A proximal fitting 36 of extension member 32 is maneuverable by a medical practitioner. In one embodiment, extension member 32 runs through the center of expandable member 16 and/or 26 and distal segment 34 that extends distally beyond the most distal expandable member. Extension member 32 may be attached to a movable proximal fitting 36 used to control deflection of expandable members 16 or 26, as is more fully explained herein.

Figure 5:
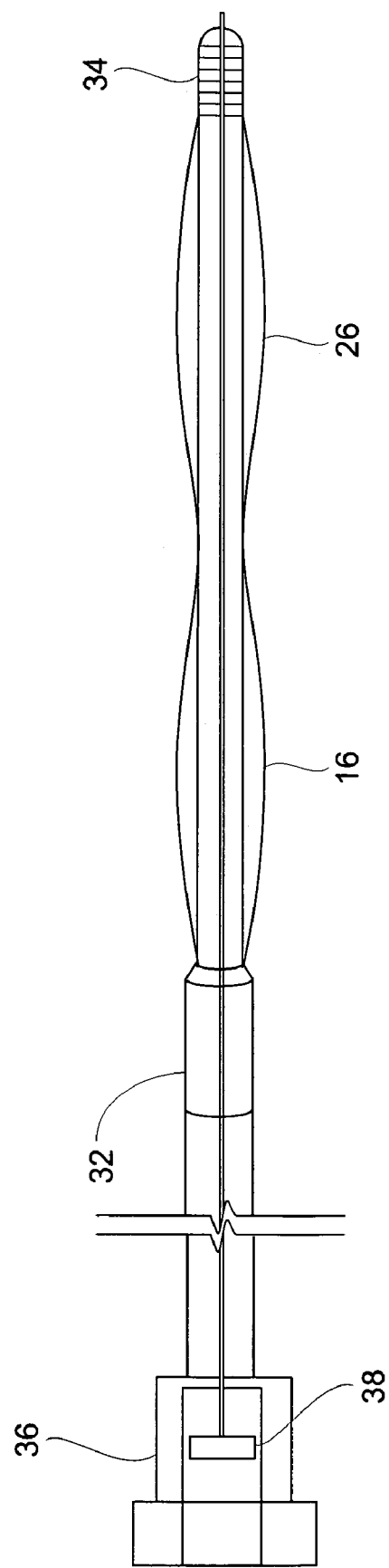
FIG. 5 illustrates a lateral view of the deflection mechanism of the invention.

Referring to FIG. 5, expandable members 16 and 26 may be initially rolled or folded around extension member 32. Expandable members 16 and 26 can be attached to a deflection mechanism 38, which imparts movement of first and second expandable members 16 and 26 when positioned at the LES. In one embodiment, the deflection mechanism can be a pull wire attached to extension member 32 or first expandable member 16 and to a movable proximal fitting 36, as is well known to those skilled in the art.

Formed spring wires can be included in first expandable member 16 to assist in opening it to the deployed position. Optionally positioned proximal fitting 36 contains a variety of actuators which provide a physician control of GERD treatment apparatus 10, as more fully described hereafter. The actuators can be rocker switches, slider switches and the like, as are well known to those skilled in the art. At least portions of GERD treatment apparatus 10 may be sufficiently radiopaque in order to be visible under fluoroscopy and/or sufficiently echogenic to be visible under ultrasonography.

Figure 6A:
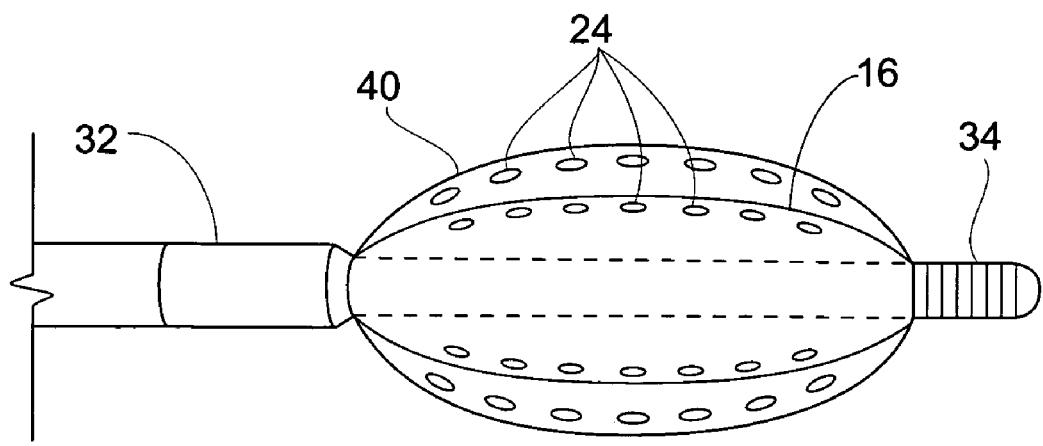
FIG. 6A illustrates a lateral view of apertures in the expandable member and conforming member of the invention.

One embodiment of GERD treatment apparatus 10 is illustrated in FIG. 6A. First expandable member 16 is made of a material that can be an insulator. For purposes of this disclosure, an insulator is a barrier to thermal or electrical energy flow. In this embodiment, expandable member 16 is substantially surrounded by a conforming member 40 which is also called a fluid conduit. Conforming member 40 receives electrolytic solution from first expandable member 16, heated or not heated, through a plurality of apertures 24 formed in first expandable member 16, and passes it to conforming member 40. In another embodiment, shown in FIG. 6B, first expandable member 16 is made of a microporous material 42 that does not include distinct apertures.

Figure 6B:
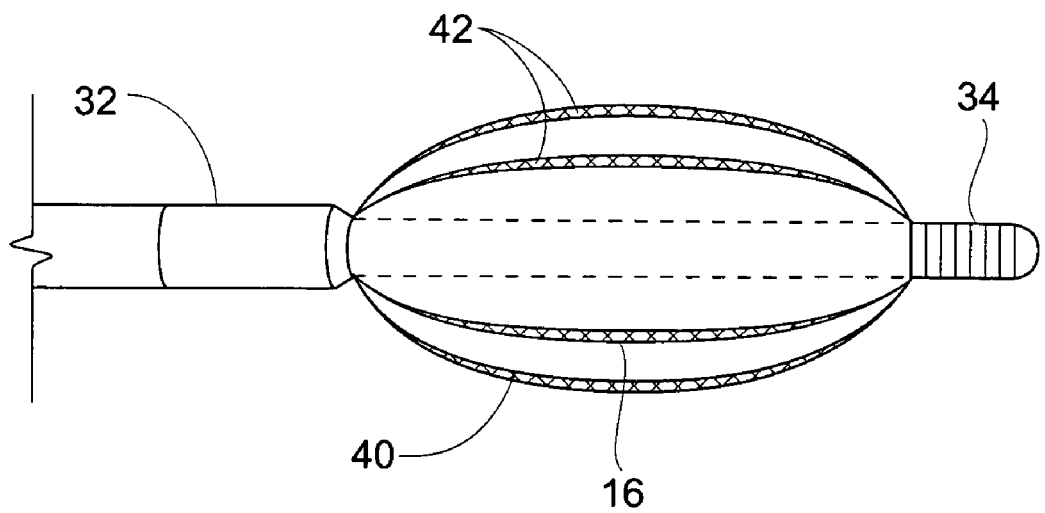
FIG. 6B illustrates a lateral view of a microporous membrane used in the fabrication of the expandable member and conforming members of the invention.

Referring to FIGS. 6A and 6B, conforming member 40 is made of a material that permits controlled delivery of the electrolytic solution to the treatment site 12 through one or more apertures 24. In another embodiment, conforming member 40 can be made of microporous material 42 that does not include distinct apertures. Extension member 32 with first and second expandable members, or alternatively with a single expandable member, is introduced into the esophagus directly, shown in FIG. 1, or through the use of another introducer such as an endoscope (not shown), as is more fully described hereafter with first and second expandable members 16 and 26 in non-deployed configurations.

Figure 7:
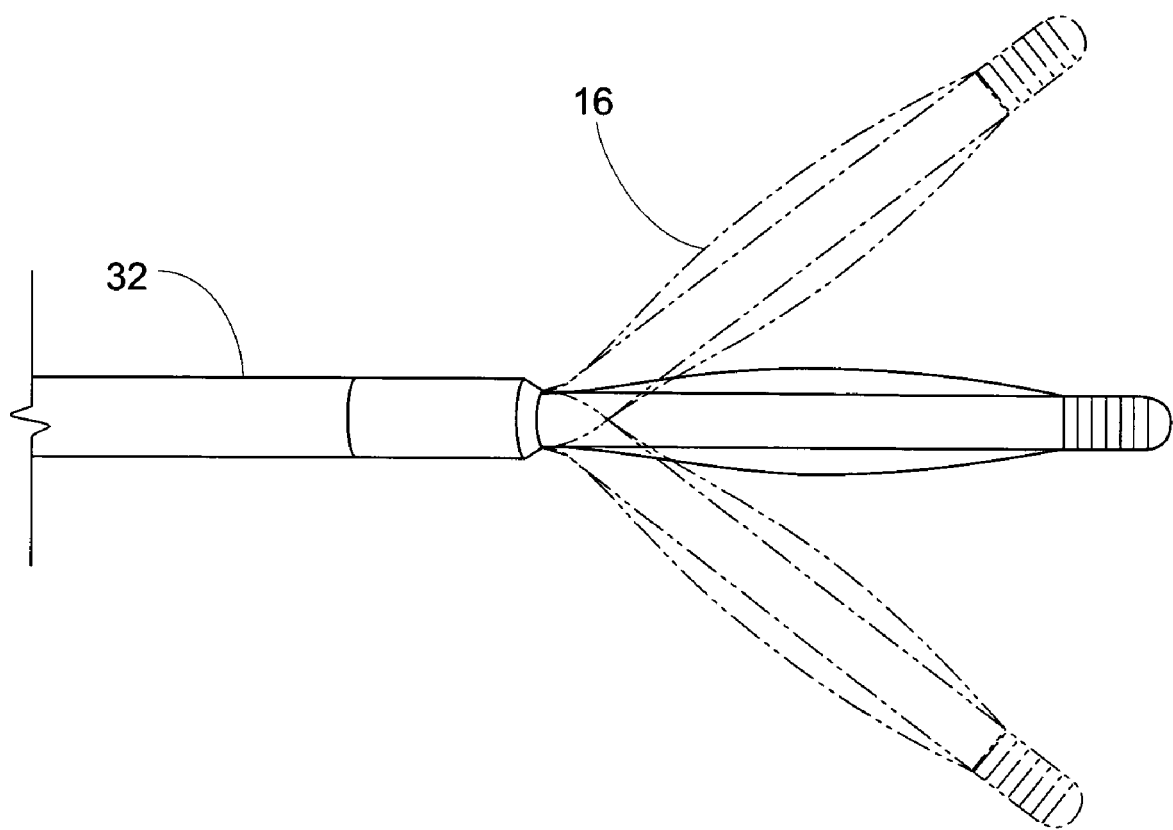
FIG. 7 is a lateral view illustrating the use of the deflection mechanism to deflect the expandable member of the present invention.

Referring to FIG. 7, first expandable member 16 can be deflected from side to side to facilitate maneuvering through the esophagus and positioning in the LES. This movement can be imparted by deflection mechanism 38.

A variety of energy sources can be coupled to the porous membrane including, (i) an RF source coupled to an RF electrode, (ii) a coherent source of light coupled to an optical fiber, (iii) an incoherent light source coupled to an optical fiber, (iv) a heated fluid coupled to a catheter with an open channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz or (xii) a microwave source. For ease of discussion for the remainder of this application, the energy source utilized is an RF source and electromagnetic energy delivery device 28 is a single or a plurality of RF electrodes 44, also described as electrodes 44. However, all of the other mentioned energy sources are equally applicable to GERD treatment apparatus 10.

Figure 8:
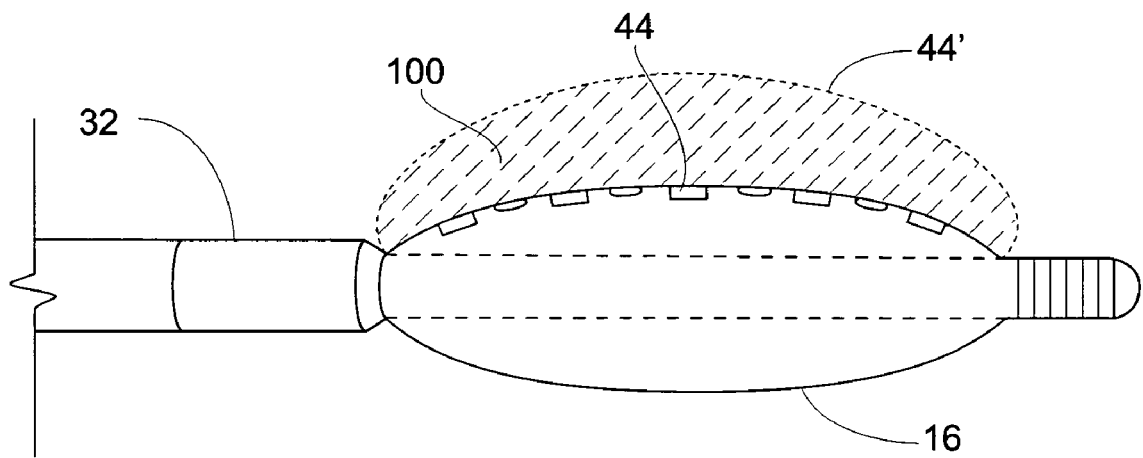
FIG. 8 is a lateral view illustrating the use of electrolytic solution to create an enhanced RF electrode.

For the case of RF energy, RF electrode 44 may be operated in either bipolar or monopolar mode with a ground pad electrode. In a monopolar mode of delivering RF energy, a single electrode 44 is used in combination with an indifferent electrode patch that is applied to the body to form the other contact and complete an electrical circuit. Bipolar operation is possible when two or more electrodes 44 are used. Multiple electrodes 44 may be used. Also, electrolytic solution serves as an enhanced RF electrode 44' when coupled with an RF electrode 44 (refer to FIG. 8).

Also when the energy source is RF, power source 30, which will now be referred to as a RF energy source 30, may have multiple channels, delivering separately modulated power to each electrode 44. This reduces preferential heating that occurs when more energy is delivered to a zone of greater conductivity and less heating occurs around electrodes 44 which are placed into less conductive tissue. If the tissue hydration or the blood infusion in the tissue is uniform, a single channel RF energy source 30 may be used to provide power for generation of lesions 14 relatively uniform in size.

Electric current flowing through targeted smooth muscle tissue causes heating due to resistance of the tissue resulting in injury to the tissue which can be sufficient to cause the death of affected cells, also known as necrosis. For ease of discussion for the remainder of this application, cell injury will include all cellular effects resulting from the delivery of energy from the electrode 44 up to and including cell necrosis. Cell injury can be accomplished as a relatively simple medical procedure with local anesthesia. In one embodiment, cell injury proceeds to a depth of approximately 1-4 mms from the surface of the mucosal layer.

Figure 9A:
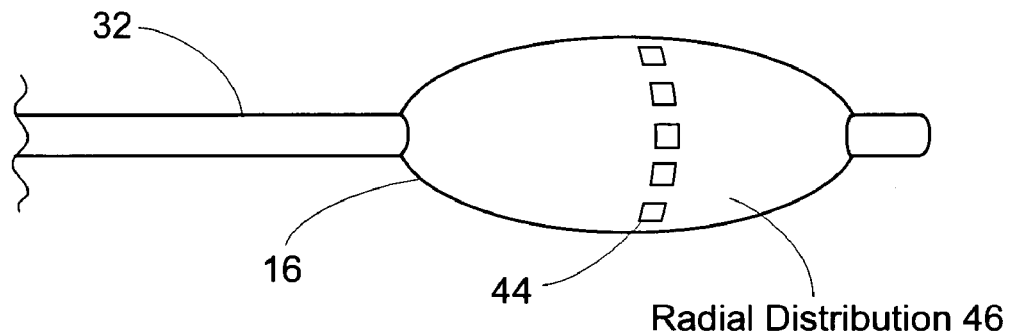
FIG. 9A is a lateral view illustrating a radial distribution of electrodes on the expandable member of the invention.
Figure 9B:
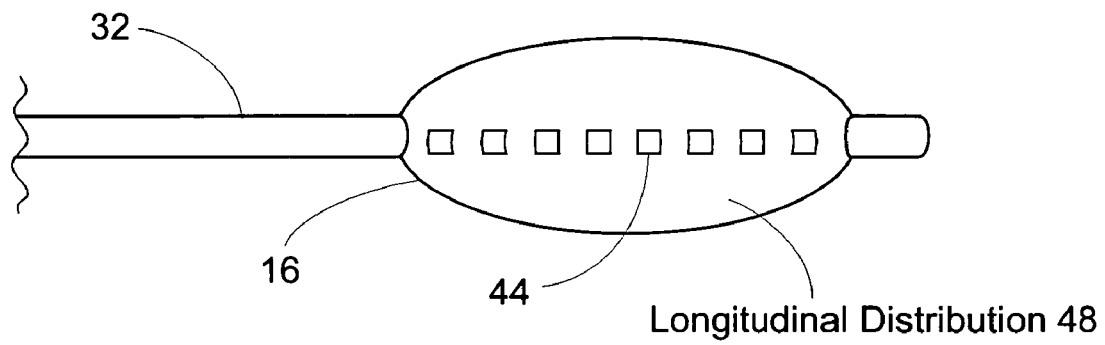
FIG. 9B is a lateral view illustrating a longitudinal distribution of electrodes on the expandable member of the invention.
Figure 9C:
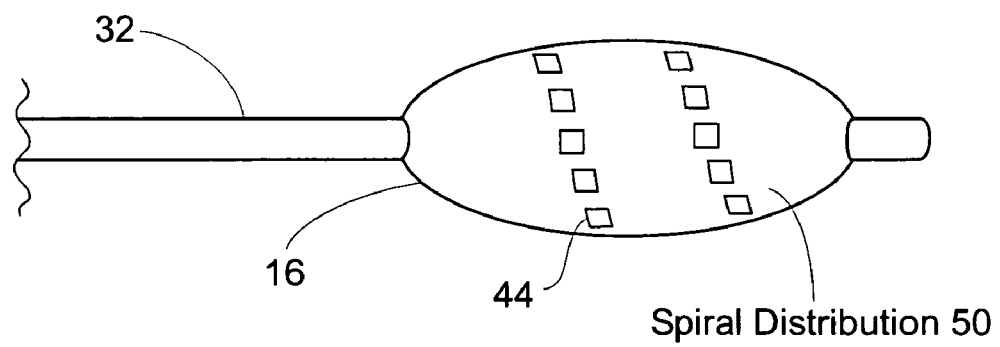
FIG. 9C is a lateral view illustrating a spiral distribution of electrodes on the expandable member of the invention.
Figure 10:
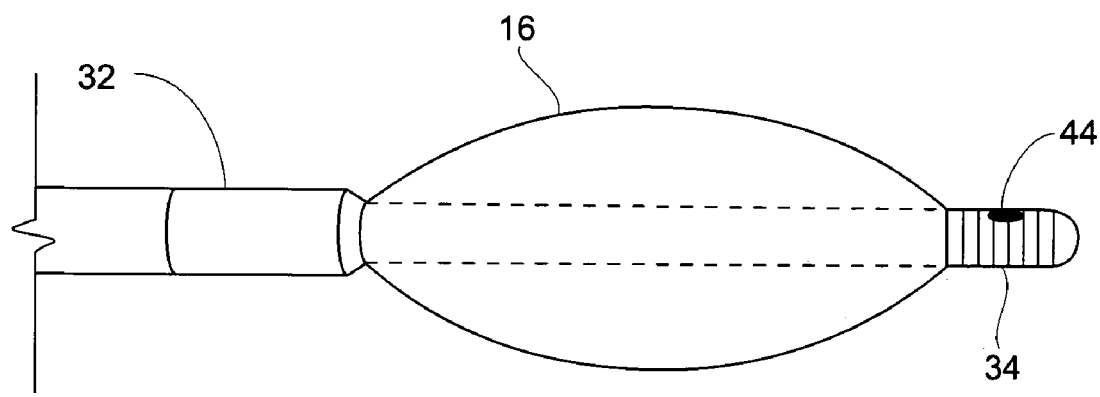
FIG. 10 is a lateral view illustrating the placement of electrodes on the distal segment of an embodiment the invention.

Referring now to FIGS. 9A-C, electrodes 44 can cover all or a portion of expandable members 16 or 26 and/or conforming member 40. Also, electrodes 44 may be distributed in a variety of patterns along an exterior or interior surface of either expandable member 16 or 26 or conforming member 40, in order to produce a desired placement and pattern of lesions 14. Typical electrode distribution patterns include, but are not limited to, a radial distribution 46 (refer to FIG. 9A) or a longitudinal distribution 48 (refer to FIG. 9B). It will be appreciated that other patterns and geometries for electrode placement, such as a spiral distribution 50 (refer to FIG. 9C) may also be suitable. In one embodiment, electrode 44 is positioned on. distal segment 34 of extension member 32 (refer to FIG. 10). These electrodes may be cooled as described hereafter. Additionally, distal segment 34 may include apertures 24 for delivery of cooling and electrolytic solution as described hereafter.

Figure 11:
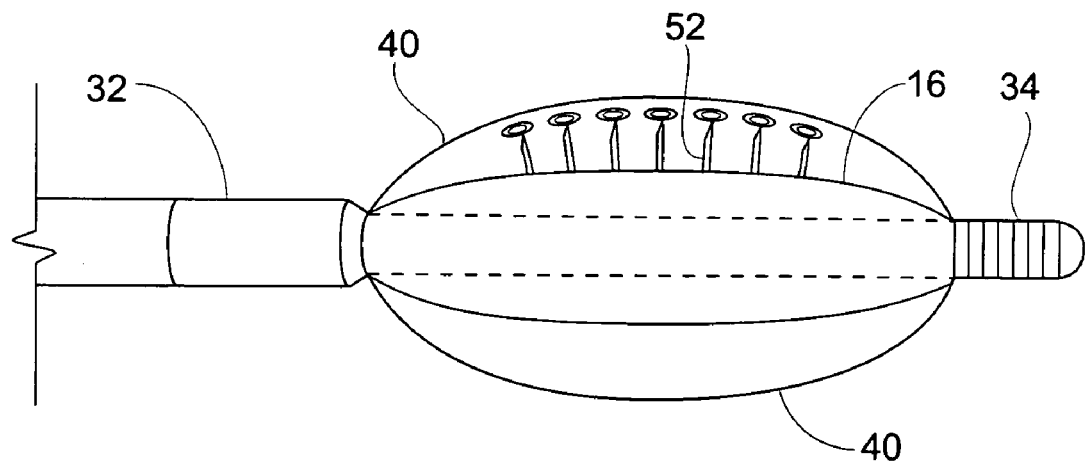
FIG. 11 is a lateral view illustrating the placement of needle electrodes on the expandable member of an embodiment the invention.
Figure 12:
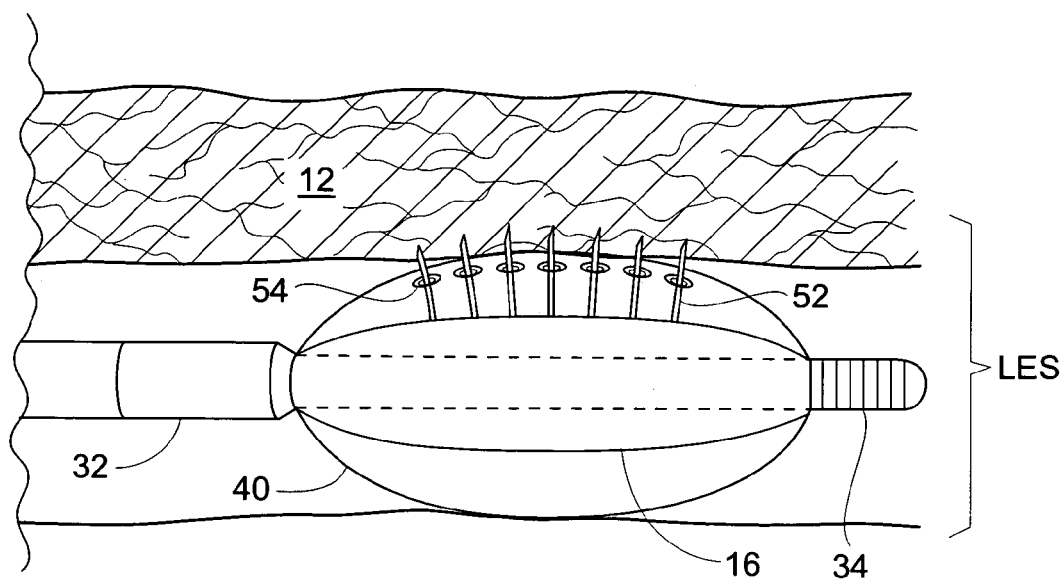
FIG. 12 is a lateral view illustrating the deployment of needle electrodes into the smooth muscle of the LES.
Figure 13:
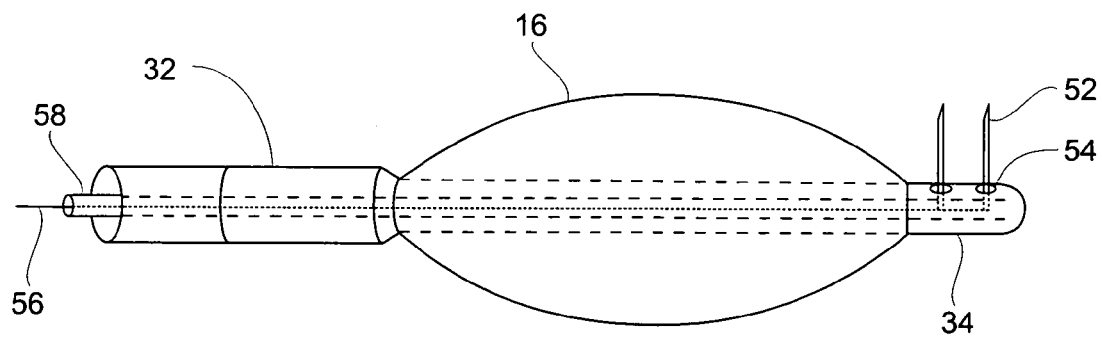
FIG. 13 is a lateral view illustrating the position of needle electrodes in the distal segment of the expandable member.

Electrodes 44 can have a variety of shapes and sizes. Possible shapes include but are not limited to circular, rectangular, conical and pyramidal. Electrode surfaces can be smooth or textured and concave or convex. Surface areas can range from 0.1 mm2 to 200 mm2. It will be appreciated that other geometries and surface areas may be equally suitable. In one embodiment, electrodes 44 can be in the shape of needles and of sufficient sharpness and length to penetrate into the smooth muscle of the esophageal wall. In this case, needle electrodes 52 are attached to expandable member 16 or 26 which is located inside conforming member 40 (refer to FIG. 11). During introduction of the GERD treatment apparatus 10 into the esophagus, needle electrodes 52 remain retracted inside conforming member 40. Once GERD treatment apparatus 10 is properly positioned at the treatment site 12, needle electrodes 52 are deployed by expansion of expandable member 16 or 26, resulting in protrusion of needle electrodes 52 through needle apertures 54 in conforming member 40 and into the smooth muscle tissue of the treatment site 12 (refer to FIG. 12). In another embodiment, distal segment 34 may also contain needle apertures 54 for protrusion of needle electrodes 52 into the smooth muscle of the esophageal wall. In this embodiment, shown in FIG. 13 needle electrodes 52 are coupled to an insulated guide wire 56 (known to those skilled in the art) which is advanced through a guide wire lumen 58 in extension member 32.

Figure 14:
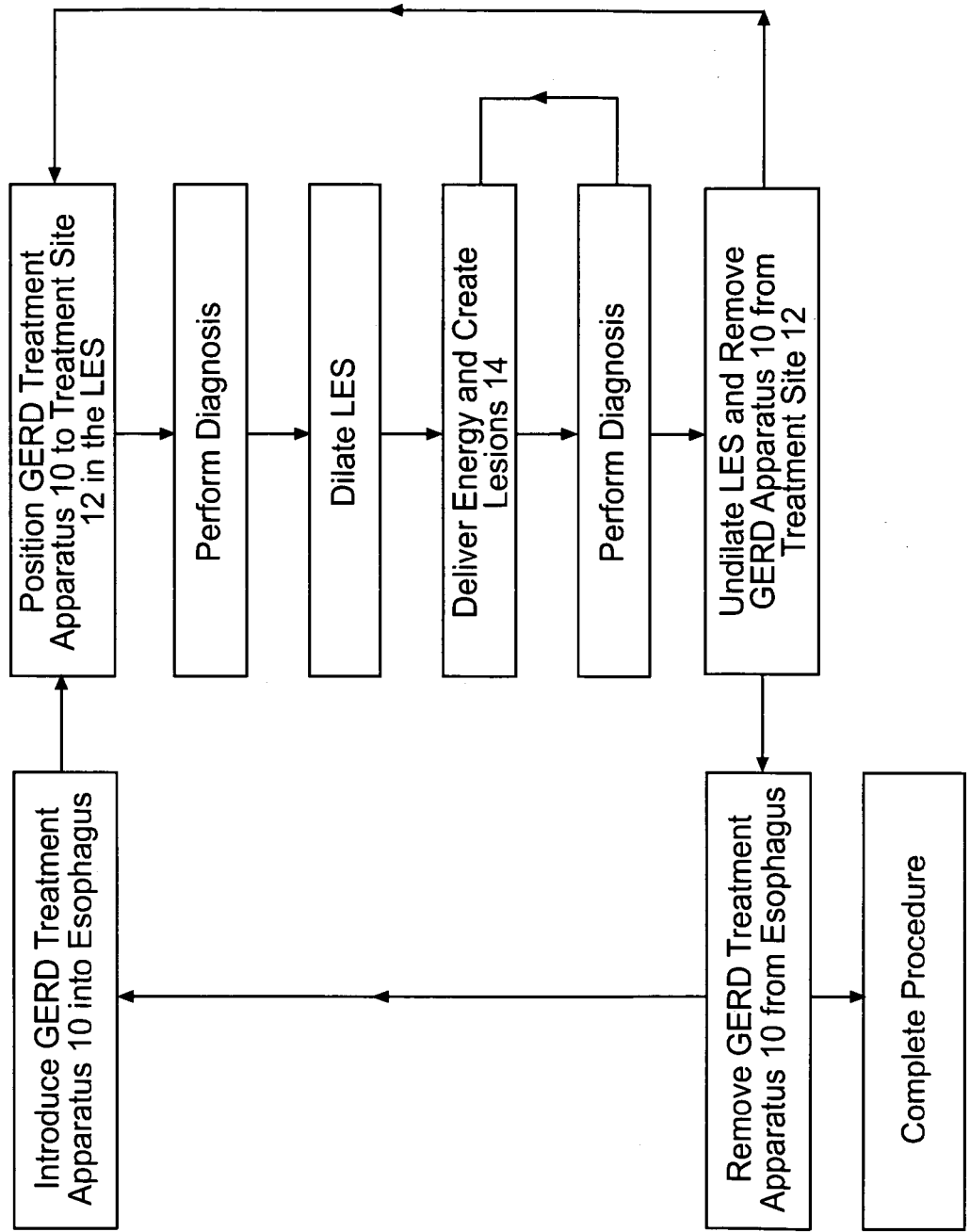
FIG. 14 is a flow chart illustrating the GERD treatment method of the current invention.

FIG. 14 is a flow chart illustrating one embodiment of the operation of GERD treatment apparatus 10. In this embodiment, GERD treatment apparatus 10 is first introduced into the esophagus under local anesthesia. GERD treatment apparatus 10 can be introduced into the esophagus by itself or through a lumen in an endoscope, such as disclosed in U.S. Pat. Nos. 5,448,990 and 5,275,608, incorporated herein by reference, or similar esophageal access device known to those skilled in the art. Expandable member 16 or 26 is expanded with the introduction of a fluid or gaseous expansion medium 22, such as an electrolytic solution, or a combination of both. This serves to temporarily dilate the esophagus sufficiently to efface a portion of or all of the folds of the LES. In an alternative embodiment, esophageal dilation and subsequent LES fold effacement can be accomplished by insufflation of the esophagus (a known technique) using gas introduced into the esophagus through a channel in the GERD treatment device, or an endoscope or similar esophageal access device as described above. Once treatment is completed, expandable members 16 or 26 are evacuated of fluid or gas and returned to their predeployed state and GERD treatment apparatus 10 is withdrawn from the esophagus. This results in the LES returning to approximately its pretreatment state and diameter.

In one embodiment, electrolytic solution is introduced into expandable member 16 or 26, causing it to become distended and be self-retained in the esophagus. Expandable member 16 or 26 can also be expanded mechanically through the use of formed spring wires (not shown) used alone or in combination with a fluid.

Electrolytic solution in expandable member 16 may be heated to a temperature, which can be modified and adjusted as necessary. For example, electrolytic solution can be heated and maintained at a temperature between about 6590° C. It can be initially introduced into first expandable member 16 at the higher temperature, or it can be heated to the higher temperature in first expandable member 16. By providing a heated electrolytic solution, there is a reduction in the amount of time needed to complete a satisfactory degree of tissue injury of targeted cells.

Figure 15A:
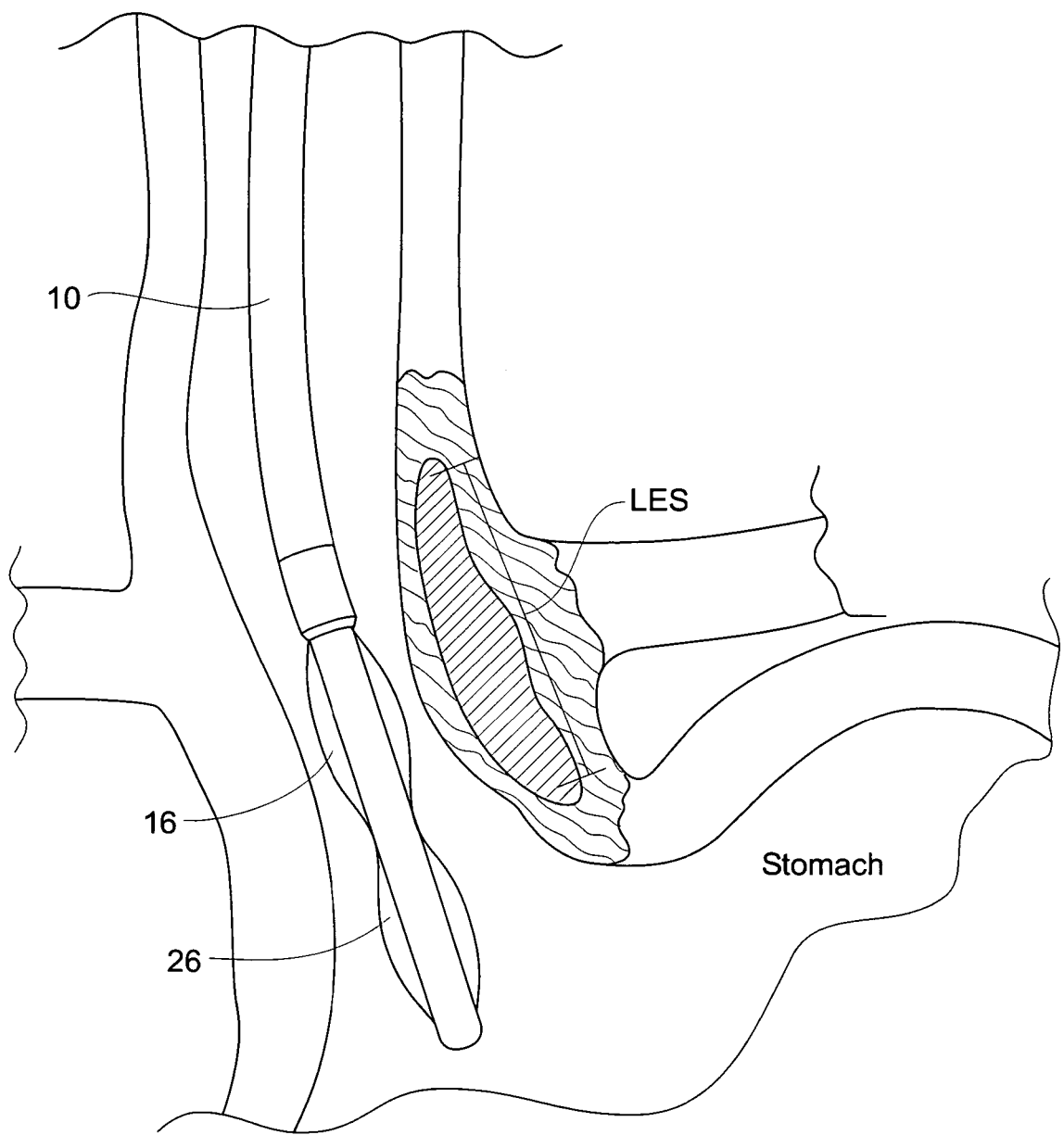
FIG. 15 A-C are lateral views which illustrate a technique for proper positioning of the GERD treatment apparatus in the LES.
Figure 15B:
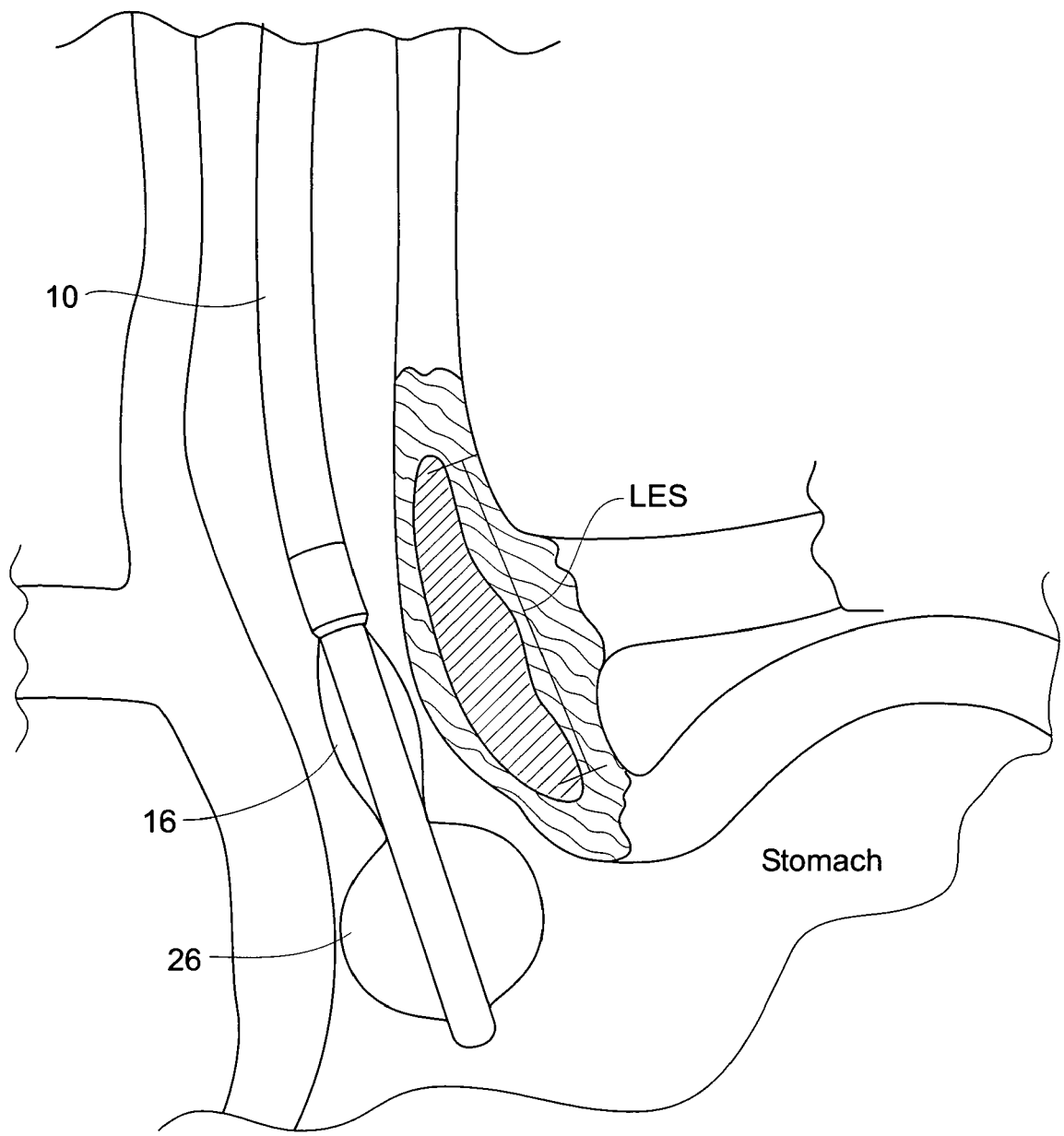
Figure 15C:
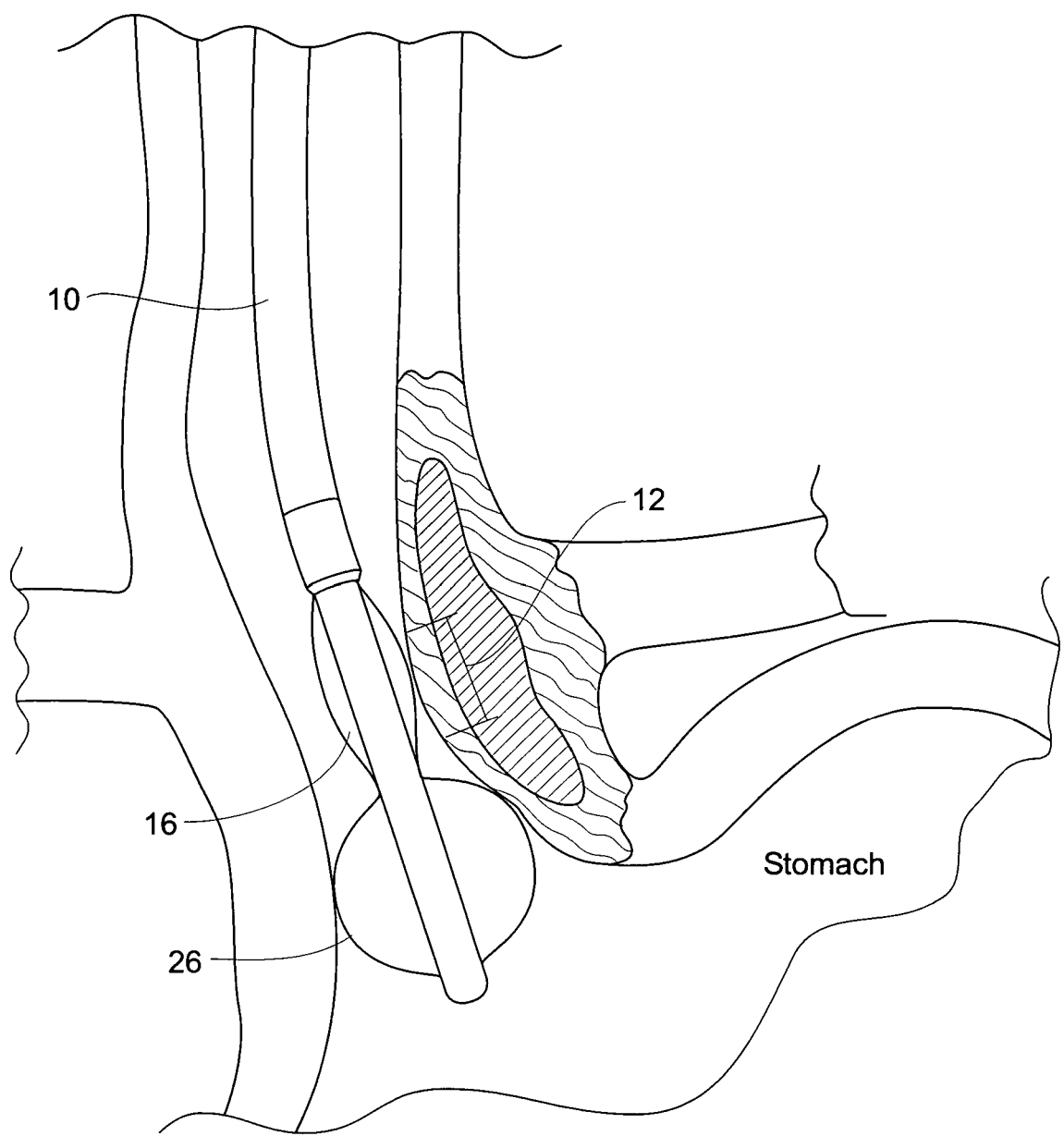

It is important to have proper positioning of the expandable members 16 and 26 and conforming member 40 in the sphincter during both diagnosis and treatment phases. This can be facilitated by the following procedure: (1) carefully advancing one or both of expandable members 16 and 26 in an unexpanded state, distal to the lower esophageal sphincter, (ii) expanding the distal one of the two expandable members and (iii) carefully withdrawing GERD treatment apparatus 10 proximally until resistance is encountered. This procedure is illustrated in FIGS. 15 A-C.

Figure 16:
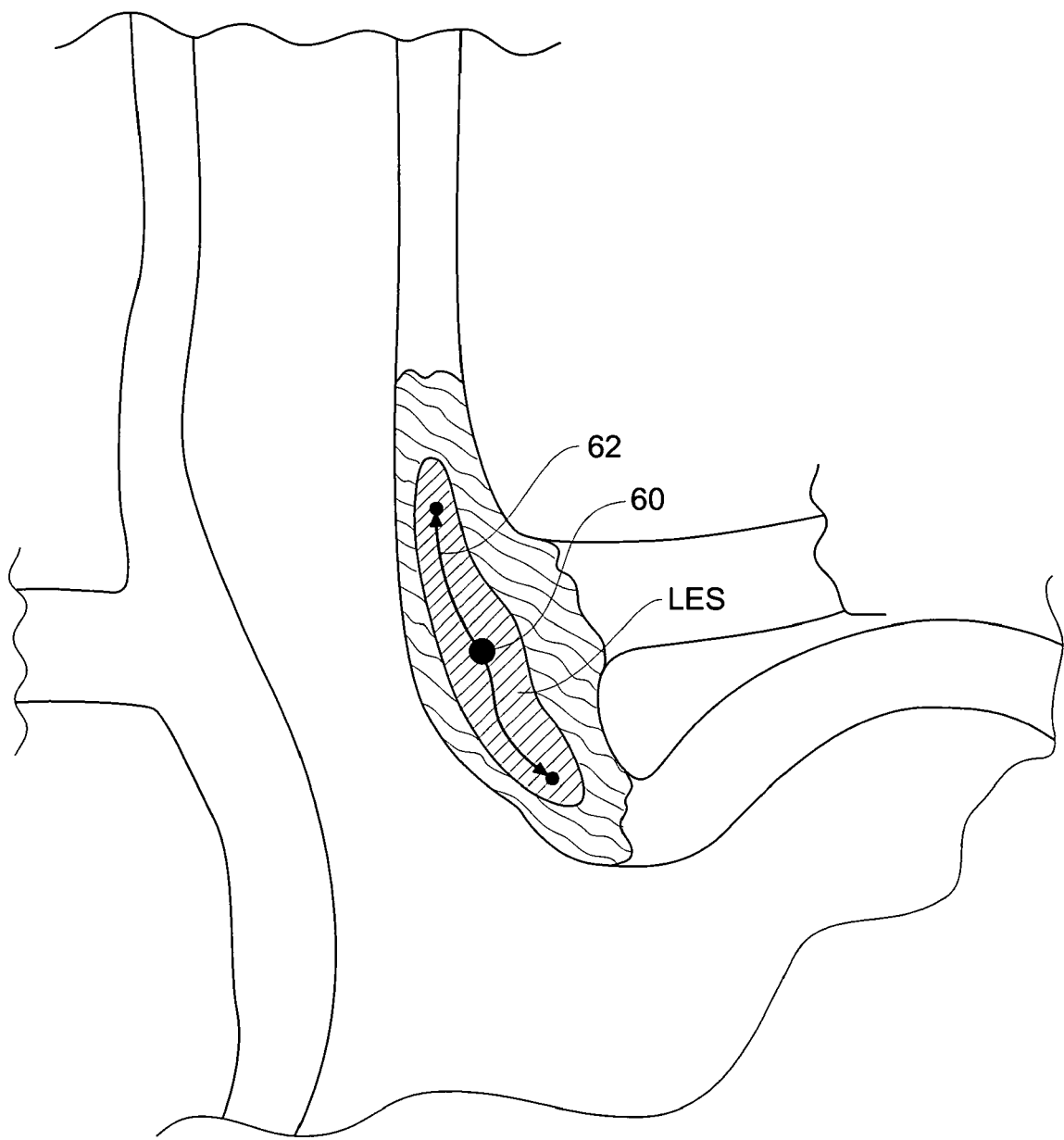
FIG. 16 is a lateral view of sphincter smooth muscle tissue illustrating electromagnetic foci and pathways for the origination and conduction of aberrant electrical signals in the smooth muscle of the lower esophageal sphincter.

The diagnostic phase then begins. This is achieved through a variety of diagnostic methods, including, but not limited to, the following: (1) visualization of the interior surface of the esophagus via an endoscope or other viewing apparatus inserted into the esophagus, (ii) visualization of the interior morphology of the esophageal wall using ultrasonography to establish a baseline for the tissue to be treated, (iii) impedance measurement to determine the electrical conductivity between the esophageal mucosal layers and GERD treatment apparatus 10 and (iv) measurement and surface mapping of the electropotential of the LES during varying time periods which may include such events as depolarization, contraction and repolarization of LES smooth muscle tissue. This latter technique is done to determine specific sites in the LES to be treated which are acting as foci 60 or pathways 62 for abnormal or inappropriate polarization and relaxation of the smooth muscle of the LES (Refer to FIG. 16).

Figure 17:
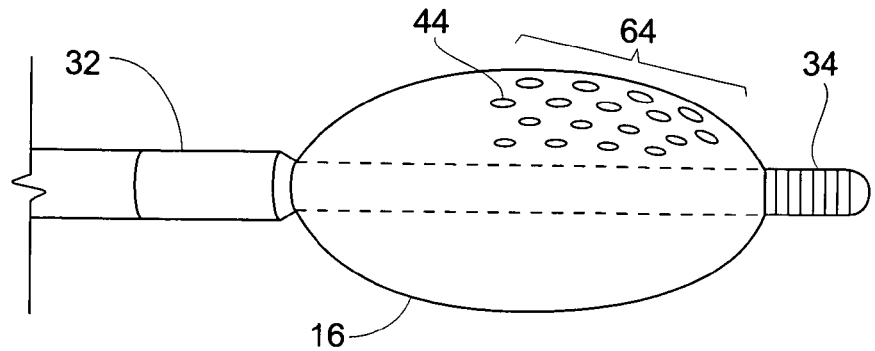
FIG. 17 is a lateral view illustrating a zone of electrodes of the current invention that comprises a flexible circuit that facilitates contact with the lower esophageal sphincter.

In the treatment phase, the delivery of energy of the targeted site can be conducted under feedback control, manually or a combination of both. Feedback control enables GERD treatment apparatus 10 to be positioned and retained in the esophagus during treatment with minimal attention by the physician. When positioned at the LES, GERD treatment apparatus 10 provides a relatively even flow of heated electrolytic solution to facilitate the cell injury process. As shown in FIG. 17, GERD treatment apparatus 10 also may have a plurality of electrodes 44 contained in zones that effectively create a flexible circuit 64 which in turn, facilitates contact of the electrode 44 with all or a portion of the interior surface areas of the LES. Electrodes 44 can be multiplexed in order to treat the targeted site or only a portion thereof. Feedback can be included and is achieved by, (1) visualization, (ii) impedance measurement, (iii) ultrasonography, (iv) temperature measurement; and, (v) sphincter contractile force measurement via manometry. The feedback mechanism permits the selected on-off switching of different electrodes 44 of the flexible circuit 64 in a desired pattern, which can be sequential from one electrode 44 to an adjacent electrode 44, or can jump around between non-adjacent electrodes 44. Individual electrodes 44 are multiplexed and volumetrically controlled by a controller.

Figure 18:
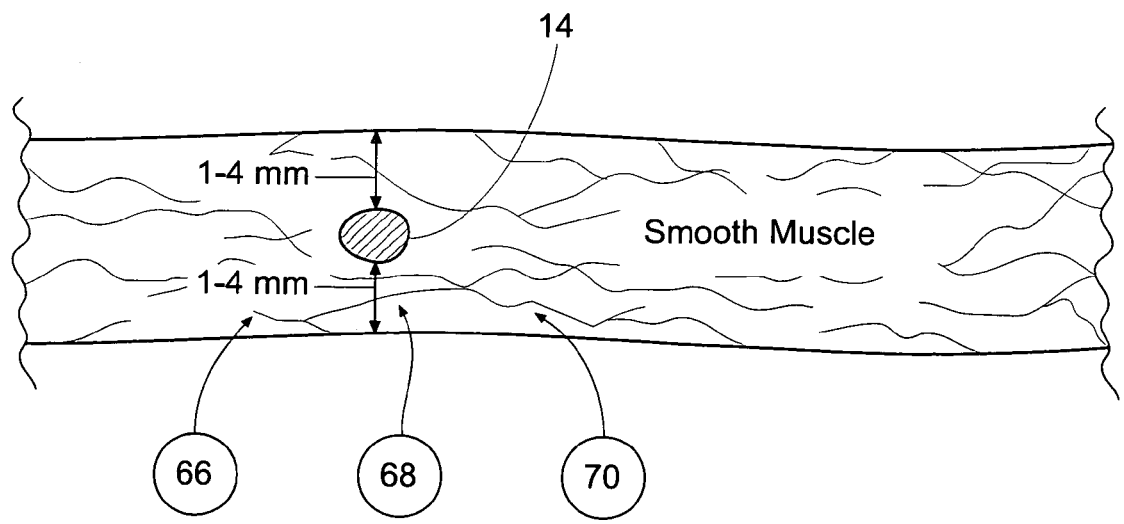
FIG. 18 is a lateral view of the esophageal wall illustrating the infiltration of tissue healing cells into a lesion in the smooth tissue of a esophageal sphincter following treatment with the GERD treatment apparatus of the present invention.
Figure 19A:
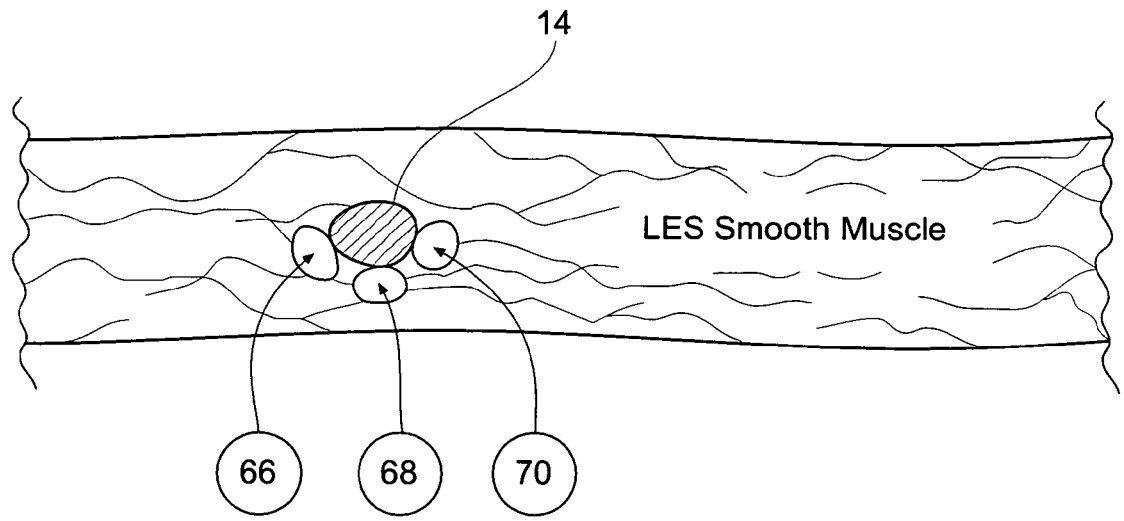
FIG. 19 is a view similar to that of FIG. 18 illustrating shrinkage of the lesion site caused by cell infiltration.
Figure 19B:
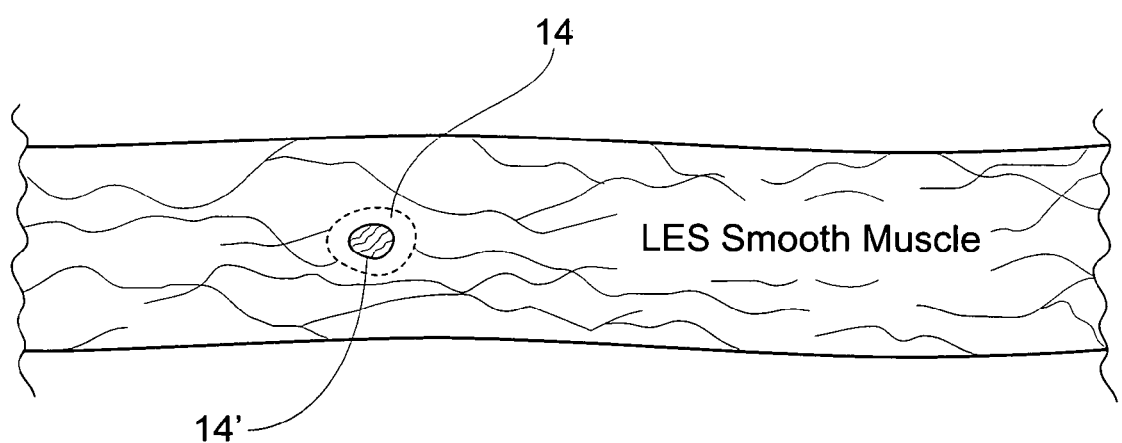
Figure 20:
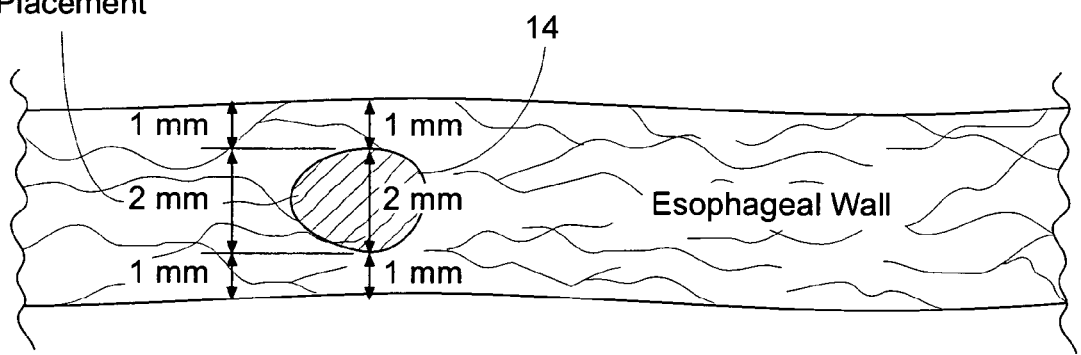
FIG. 20 is a lateral view of the esophageal wall illustrating the preferred placement of lesions in the smooth muscle layer of a esophageal sphincter.

The area and magnitude of cell injury in the LES can vary. However, it is desirable to deliver sufficient energy to the targeted treatment site 12 to be able to achieve tissue: temperatures in the range of 55-95° C. and produce lesions 14 at depths ranging from 1-4 mm from the interior surface of the LES. Typical energies delivered to the esophageal wall include, but are not limited to, a range between 100 and 50,000 joules per electrode 44. It is also desirable to deliver sufficient energy such that the resulting lesions 14 have a sufficient magnitude and area of cell injury to cause an infiltration of lesion 14 by fibroblasts 66, myofibroblasts 68, macrophages 70 and other cells involved in the tissue healing process (refer to FIG. 18). As shown in FIGS. 19A and B, these cells cause a contraction of tissue around lesion 14, decreasing its volume and, or altering the biomechanical properties at lesion 14 so as to result in a lightening of LES. These changes are reflected in transformed lesion 14' shown in 19 B. The diameter of lesions 14 can vary between 0.1 to 4 mm. It is preferable that lesions 14 are less than 4 mm in diameter in order to reduce the risk of thermal damage to the mucosal layer. In one embodiment, a 2 mm diameter lesion 14 centered in the wall of the smooth muscle provides a 1 mm buffer zone to prevent damage to the mucosa, submucosa and adventia, while still allowing for cell infiltration and subsequent tightening on approximately 50% of the thickness of the wall of the smooth muscle (refer to FIG. 20).

In one embodiment, GERD treatment apparatus 10 conforms tightly with the interior of the esophagus so that all, or nearly all, of the interior circumference of a desired segment of the LES is in contact with a surface of conforming member 40. Conforming member 40 is fitted into the entire LES and expandable member 16 does not have to be moved about the esophagus to complete the treatment. Alternatively, GERD treatment apparatus 10 may not entirely fill the esophagus, and GERD treatment apparatus 10 is then moved about the esophagus in order to treat all of the esophagus, or those sections where tightening of the lower esophageal sphincter is desired.

Conforming member 40 is made of a material that substantially conforms to the surface of the LES and, or other sphincters. This provides better conformity than the mere use of expandable member 16. As a result, the delivery of treatment energy to the LES is enhanced. Energy delivery may also be enhanced by use of a conducting surface 72 which may cover all, or part of, the exterior of conforming member 40. The surface of conforming member 40 can be made conductive by a variety of means including, but not limited to chemical coating with a conductive material, implantation with conductive ions and application of a conductive film.

Conforming member 40 can have a thickness in the range of about 0.01 to 2.0 cm. Conforming member 40 can be made of a foam type material. Suitable materials include, but are not limited to, knitted polyester, continuous filament polyester, polyester-cellulose, rayon, polyamide, polyurethane, polyethylene, silicone, and the like. Suitable commercial foams include, (i) Opcell, available from Sentinel Products Corp., Hyannis, Mass. and (ii) UltraSorb, HT 4201 or HT 4644MD from Wilshire Contamination Control, Carlsbad, Calif. Conforming member 40 has characteristics that make it particularly moldable and formable to irregular surfaces. In one embodiment, conforming member 40 is made of an open cell foam, or alternatively it can be a thermoplastic film such as polyurethane, low density polyethylene, or it may be a silicone. Additionally, conforming member 40 can be capable of extruding conductive materials from conforming member 40 itself.

Figure 21:
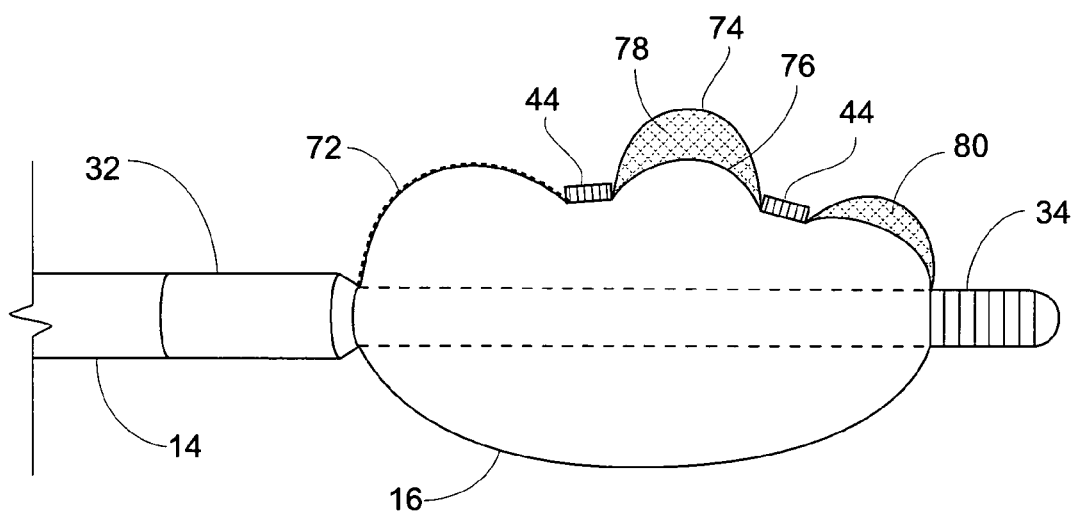
FIG. 21 is a lateral view illustrating the creation of zones of decreased porosity by sealed conforming members of an embodiment of the present invention.

FIG. 21 illustrates that conforming member 40 can be created by sealing two smaller conforming members 74 and 76 together. Smaller conforming members 74 and 76 are sealed together between individual electrodes 44. This creates a pocket or zone 78. Zone 78 has a lower porosity for the flow of electrolytic solution than non-zone sections 80, e.g., all other sections of conforming member 40 which do not include a zone 78 with an associated electrode 44. The porosity of non-zone sections 80 is greater than the porosity of zones 78.

Figure 22:
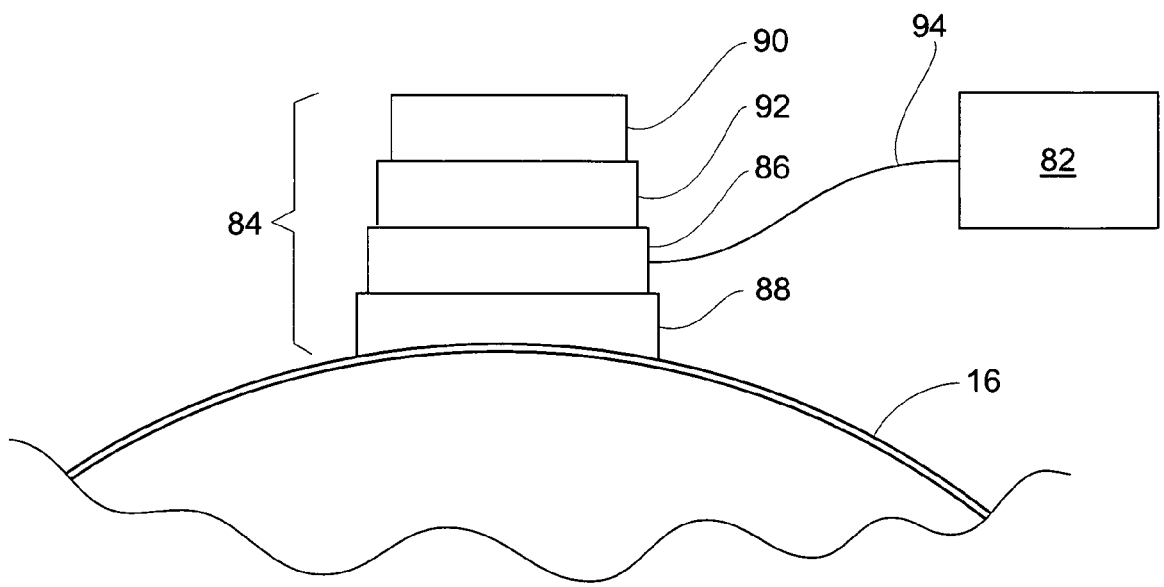
FIG. 22 is a lateral view illustrating the ultrasound transducer, ultrasound lens and ultrasound power source of an embodiment of the present invention.
Figure 23A:
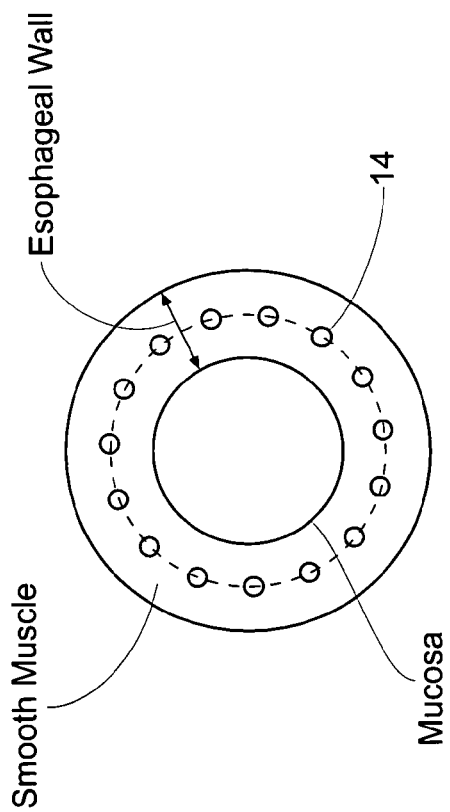
FIGS. 23A-23D are lateral views of the esophageal wall illustrating various patterns of lesions created by the apparatus of the present invention.
Figure 23B:
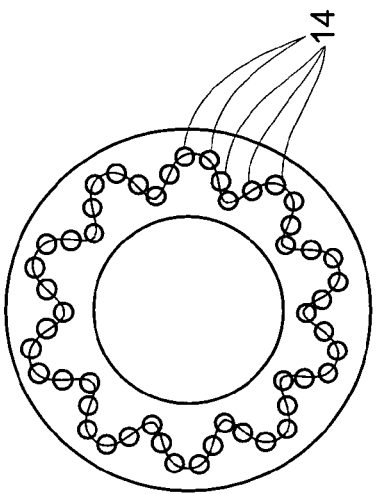
Figure 23C:
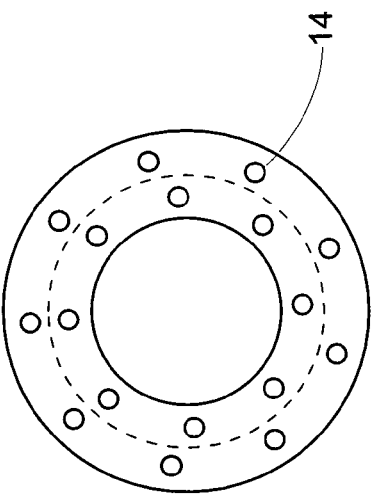
Figure 23D:
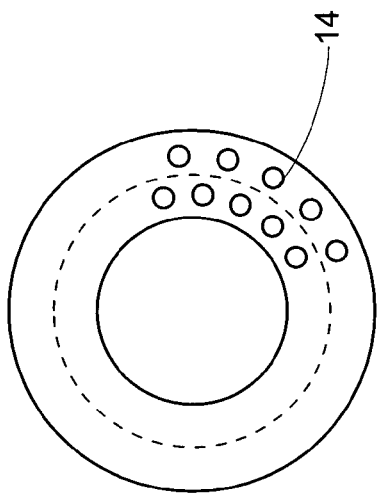

From a diagnostic standpoint, it is desirable to image the interior surface 18 and wall of the LES including the size and position of created lesions 14. It is desirable to create a map of these structures which can input to a controller and used to direct the delivery of energy to the treatment site. Referring to FIG. 22, this can be accomplished through the use of ultrasonography (a known procedure) which involves the use of an ultrasound power source 82 coupled to one or more ultrasound transducers 84 that are positioned in or on expandable member 16 or 26 or conforming member 40. An output is associated with ultrasound power source 82 and RF energy source 30.

Each ultrasound transducer 84 can include a piezoelectric crystal 86 mounted on a backing material 88 that is in turn attached to expandable members 16 or 26 or conforming member 40. An ultrasound lens 90, fabricated on an electrically insulating material 92, is mounted over the piezoelectric crystal 86 The piezoelectric crystal 86 is connected by electrical leads 94 to ultrasound power source 82. Each ultrasound transducer 84 transmits ultrasound energy through conforming member 40 or expandable members 16 or 26 into adjacent tissue. Ultrasound transducers 84 can be in the form of an imaging probe such as Model 21362, manufactured and sold by Hewlett Packard Company, Palo Alto, Calif. In one embodiment, two ultrasound transducers 84 are positioned on opposite sides of expandable member 16 to create an image depicting the size and position of lesion 14 in the LES.

It is desirable that lesions 14 are predominantly located in the smooth muscle layer of esophageal wall at the depths ranging from 1 to 4 mms from the interior surface of the sphincter. However, lesions 14 can vary both in number and position within the sphincter wall. It may be desirable to produce a pattern of multiple lesions 14 within the esophageal smooth muscle in order to obtain a selected degree of tightening of the LES. Typical lesion patterns shown in FIGS. 23 A-D include but are not limited to, (i) a concentric circle of lesions 14 all at fixed depth in the smooth muscle layer evenly spaced along the radial axis of the LES, (ii) a wavy or folded circle of lesions 14 at varying depths in the smooth muscle layer evenly spaced along the radial axis of the LES, (iii) lesions 14 randomly distributed at varying depths in the smooth muscle, but evenly spaced in a radial direction; and, (iv) an eccentric pattern of lesions 14 in one or more radial locations in the smooth muscle wall. Accordingly, the depth of RF and thermal energy penetration in the lower esophageal sphincter is controlled and selectable. The selective application of energy to the lower esophageal sphincter may be the even penetration of RF energy to the entire targeted site, a portion of it, or applying different amounts of RF energy to different sites depending on the condition of the sphincter. If desired, the area of cell injury can be substantially the same for every treatment event.

Figure 24:
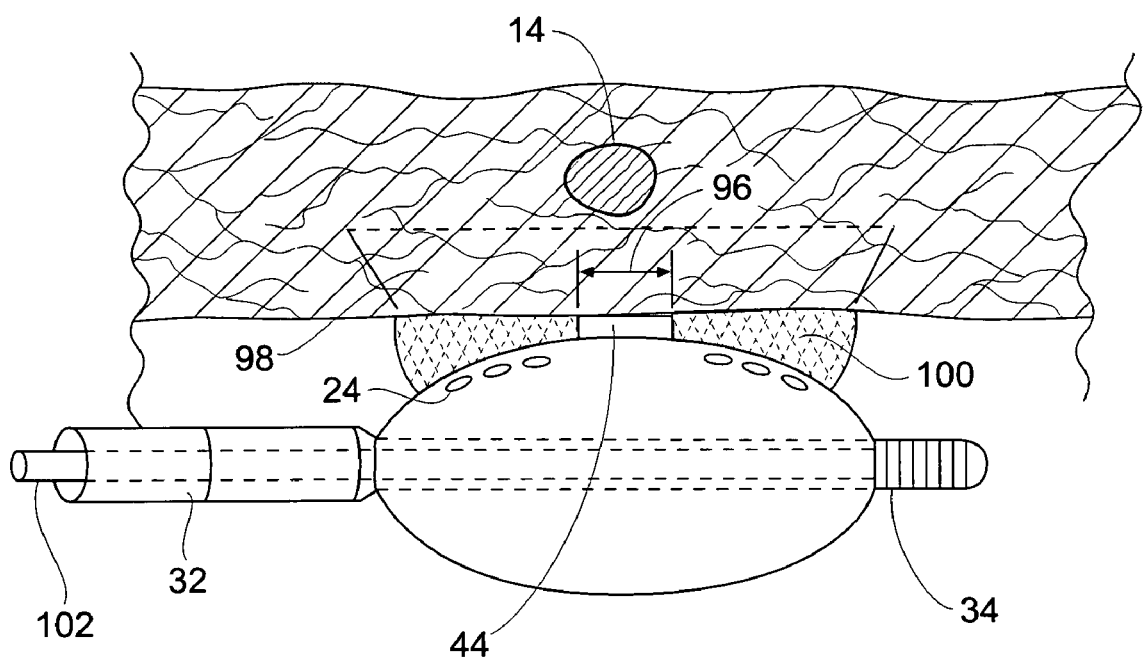
FIG. 24 is a lateral view of the esophageal wall illustrating the delivery of cooling fluid to the electrode-tissue interface and the creation of cooling zones.
Figure 25:
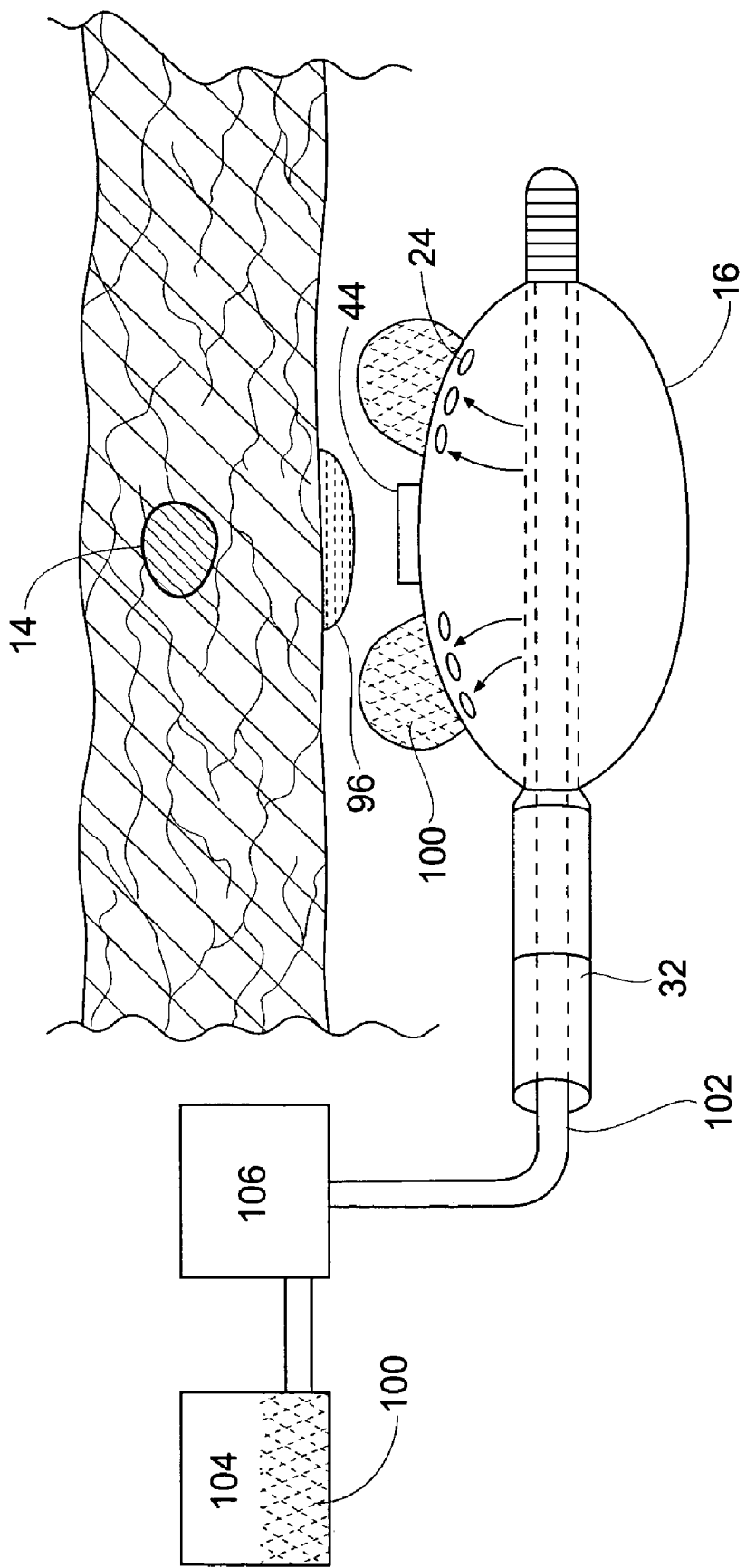
FIG. 25 depicts the flow path, fluid connections and control unit employed to deliver fluid to the electrode-tissue interface and electrodes.

Referring to FIG. 24, it may be desirable to cool all or a portion of the area near the electrode-tissue interface 96 before during and after the delivery of energy in order to reduce the degree and area of cell injury. Specifically the use of cooling preserves the mucosal layers and protects or otherwise reduces the degree of cell damage to cooled zone 98 in the vicinity of the lesion 14. This can be accomplished through the use of a cooling fluid 100 that weeps out of the expandable members 16 and 26 or conforming member 40 which is in fluid communication with a continuous lumen 102 in extension member 32 that is, in turn, in fluid communication with fluid reservoir 104 and a control unit 106, whose operation will be described hereafter that controls the delivery of the fluid (Refer to FIG. 25). All or only a portion of electrode 44 may also be cooled.

Figure 26:
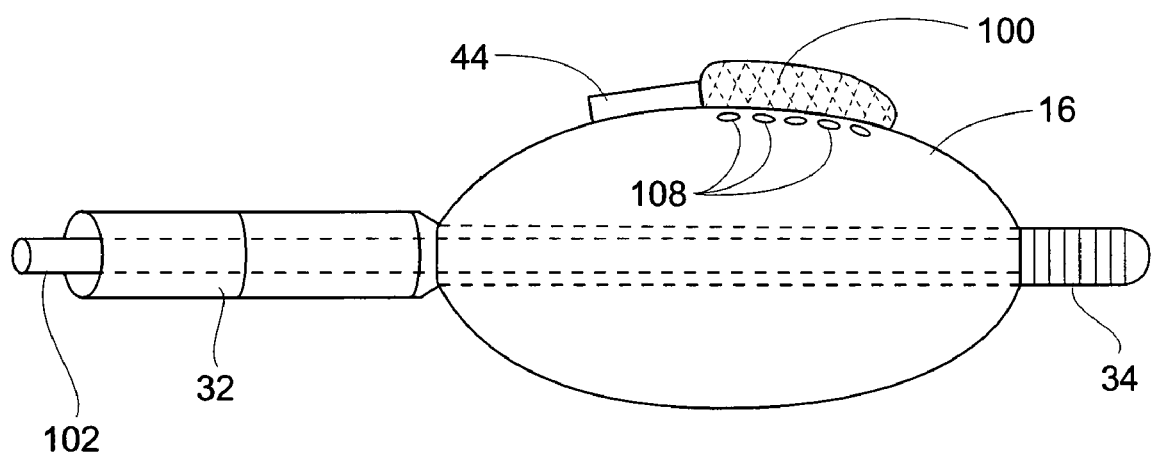
FIG. 26 is a lateral view illustrating the placement of cooling apertures adjacent to electrodes in the expandable member.

Similarly, it may also be desirable to cool all or a portion of the electrode 44. The rapid delivery of heat through electrode 44, may result in the build up of charred biological matter on electrode 44 (from contact with tissue and fluids e.g. blood) that impedes the flow of both thermal and electrical energy from electrode 44 to adjacent tissue and causes an electrical impedance rise beyond a cutoff value set on RF energy source 30. A similar situation may result from the desiccation of tissue adjacent to electrode 44. Cooling of the electrode 44 can be accomplished by cooling fluid 100 that weeps out of expandable members 16 and/or 26 and conforming member 40 as described previously. In another embodiment, expandable member 16 may contain a plurality of cooling apertures 108 adjacent or directed toward electrode 44 to enhance the flow of cooling solution and, or cooling rate of electrode 44 and adjacent tissue (refer to FIG. 26).

Figure 27:
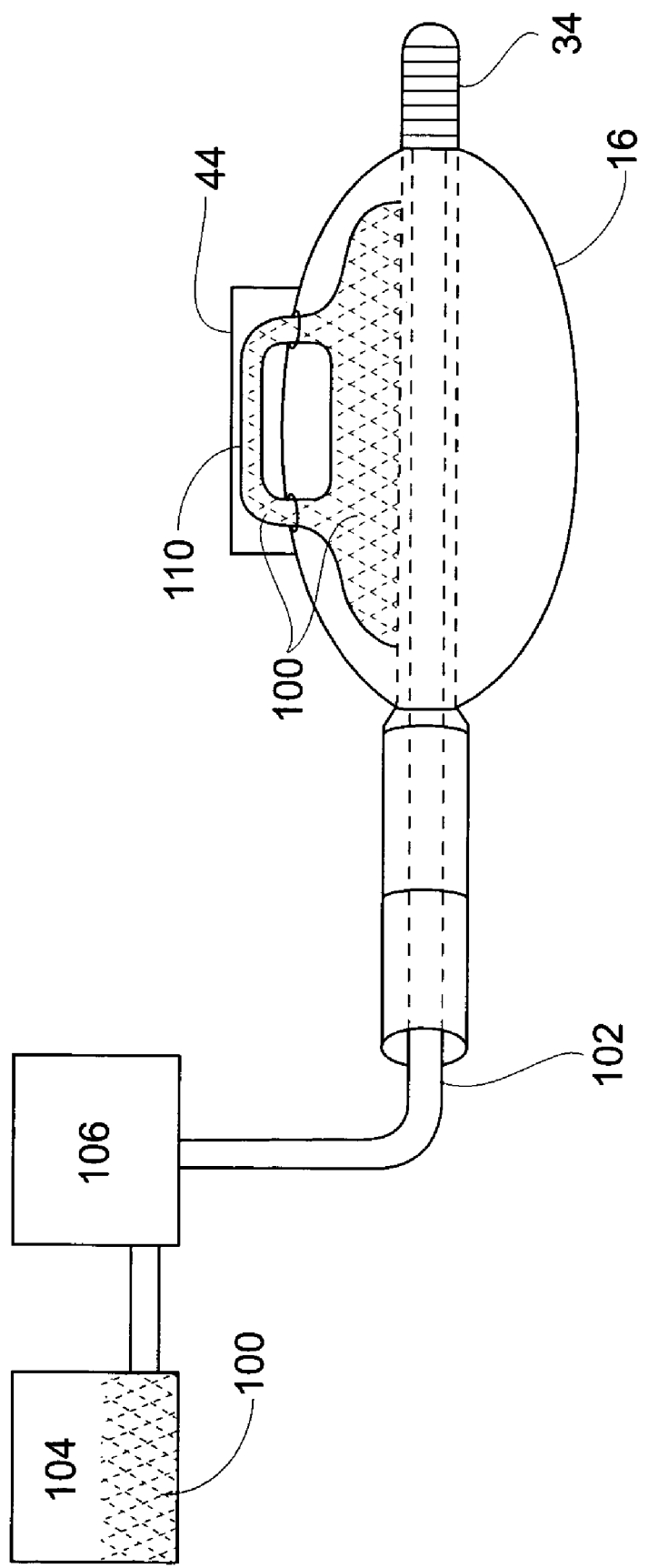
FIG. 27 depicts the flow path, fluid connections and control unit employed to deliver fluid to the RF electrodes.

Referring now to FIG. 27, electrode 44 may also be cooled via a fluid channel 110 in electrode 44 that is in fluid communication with fluid reservoir 104 and control unit 106 via the continuous lumen 102 in extension member 32 as described previously.

Figure 28:
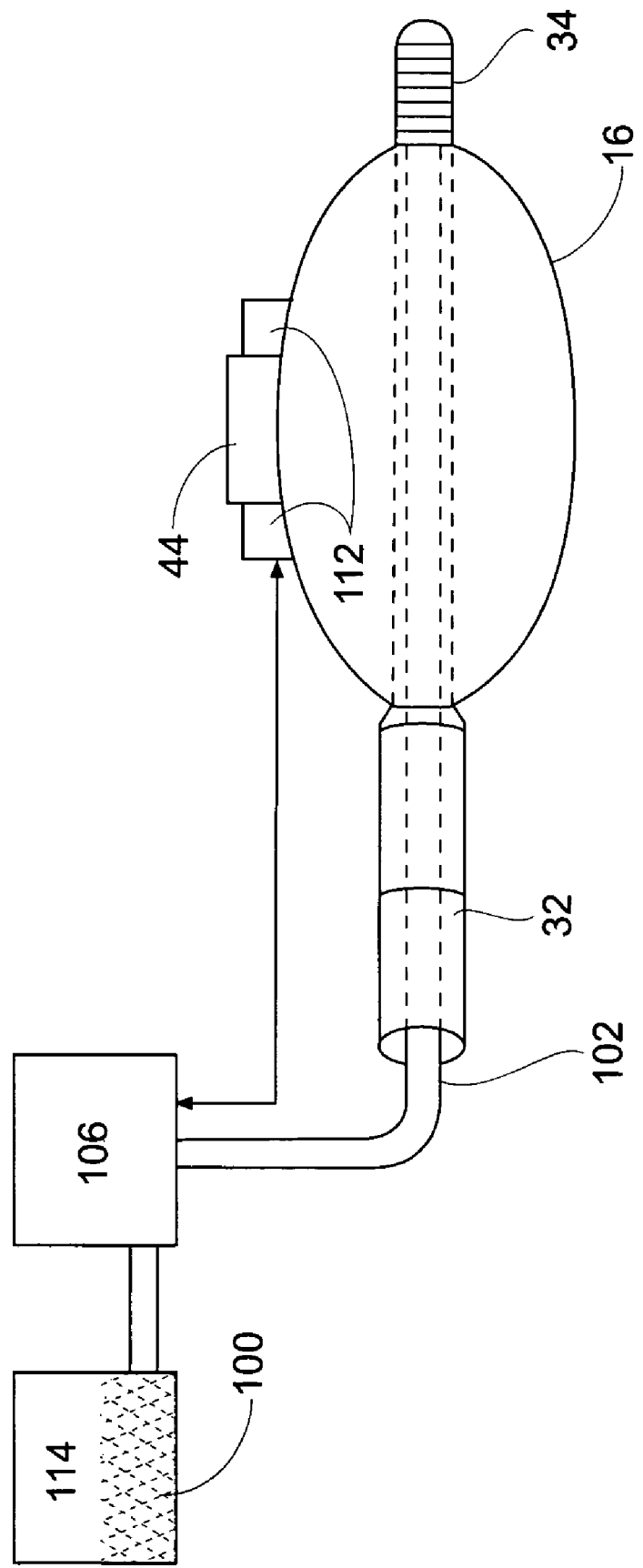
FIG. 28 is an enlarged lateral view illustrating the placement of sensors on the expandable member.

As shown in FIG. 28. one or more sensors 112 may be positioned adjacent or on electrode 44 for sensing the temperature of esophageal tissue at treatment site 12. More specifically, sensors 112 permit accurate determination of the surface temperature of the esophagus at electrode-tissue interface 96. This information can be used to regulate both the delivery of energy and cooling solution to the interior surface of the esophagus. In various embodiments sensors 112 can be positioned at any position on expandable members 16 and 26 and conforming member 40. Suitable sensors that may be used for sensor 112 include: thermocouples, fiber optics, resistive wires, thermocouple IR detectors, and the like. Suitable thermocouples for sensor 112 include: T type with copper constantene, J type, E type and K types as are well known to those skilled in the art.

Temperature data from sensors 112 are fed back to control unit 106 and through an algorithm which is stored within a microprocessor memory of control unit 106. Instructions are sent to an electronically controlled micropump (not shown) to deliver fluid through the fluid lines at the appropriate flow rate and duration to provide control temperature at the electrode-tissue interface 96 (refer to FIG. 28).

The reservoir of control unit 106 may have the ability to control the temperature of the cooling fluid 100 by either cooling the fluid or heating the fluid. Alternatively, a fluid reservoir 104 of sufficient size may be used in which the cooling fluid 100 is introduced at a temperature at or near that of the normal body temperature. Using a thermally insulated reservoir 114, adequate control of the tissue temperature may be accomplished without need of refrigeration or heating of the cooling fluid 100. Cooling fluid 100 flow is controlled by control unit 106 or another feedback control system (described herein) to provide temperature control at the electrode-tissue interface 96.

A second diagnostic phase may be included after the treatment is completed. This provides an indication of lower esophageal tightening treatment success, and whether or not a second phase of treatment, to all or only a portion of the esophagus, now or at some later time, should be conducted. The second diagnostic phase is accomplished through, (1) visualization, (ii) measuring impedance, (iii) ultrasonography or (iv) temperature measurement, (v) measurement of LES tension and contractile: force via manometry.

Figure 29:
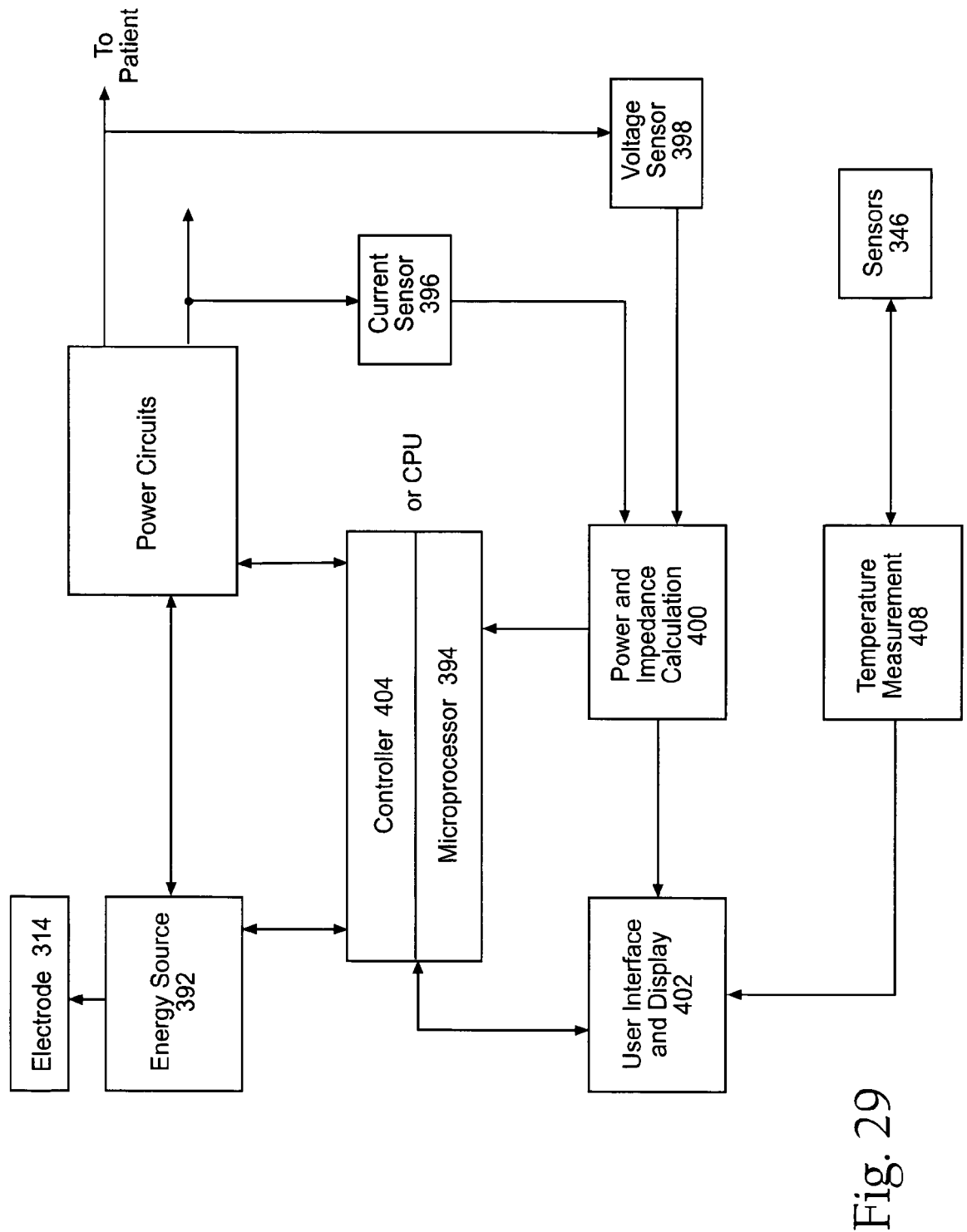
FIG. 29 depicts a block diagram of the feed back control system that can be used with the GERD treatment apparatus as shown in FIG. 3.

In one embodiment, GERD treatment apparatus 10 is coupled to an open or closed loop feedback system. Referring now to FIG. 29, an open or closed loop feedback system couples sensor 346 to energy source 392. In this embodiment, RF electrode 314 its one or more RF electrodes 314.

The temperature of the tissue, or of RF electrode 314 is monitored, and the output power of energy source 392 adjusted accordingly. The physician can, if desired, override the closed or open loop system. A microprocessor can be included and incorporated in the closed or open loop system to switch power on and off, as well as modulate the power. The closed loop system utilizes a microprocessor 394 to serve as a controller, monitor the temperature, adjust the RF power, analyze at the result, refeed the result, and then modulate the power.

With the use of sensor 346 and the feedback control system a tissue adjacent to RF electrode 314 can be maintained at a desired temperature for a selected period of time without impeding out. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output in an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of energy when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output in an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 402 includes operator controls and a display. Controller 404 can be coupled to imaging systems, including but not limited to ultrasound, CT scanners, X-ray, MRI, mammographic X-ray and the like. Further, direct visualization and tactile imaging can be utilized.

The output of current sensor 396 and voltage sensor 398 is used by controller 404 to maintain a selected power level at RF electrode 314. The amount of RF energy delivered controls the amount of power. A profile of power delivered can be incorporated in controller 404 and a preset amount of energy to be delivered may also be profiled.

Circuitry, software and feedback to controller 404 result in process control, and the maintenance of the selected power setting that is independent of changes in voltage or current, and used to change, (i) the selected power setting, (ii) the duty cycle (on-off time), (iii) bipolar or monopolar energy delivery and (iv) fluid delivery, including flow rate and pressure. These process variables are controlled and varied, while maintaining the desired delivery of power independent of changes in voltage or current, based on temperatures monitored at sensor 346.

Figure 30:
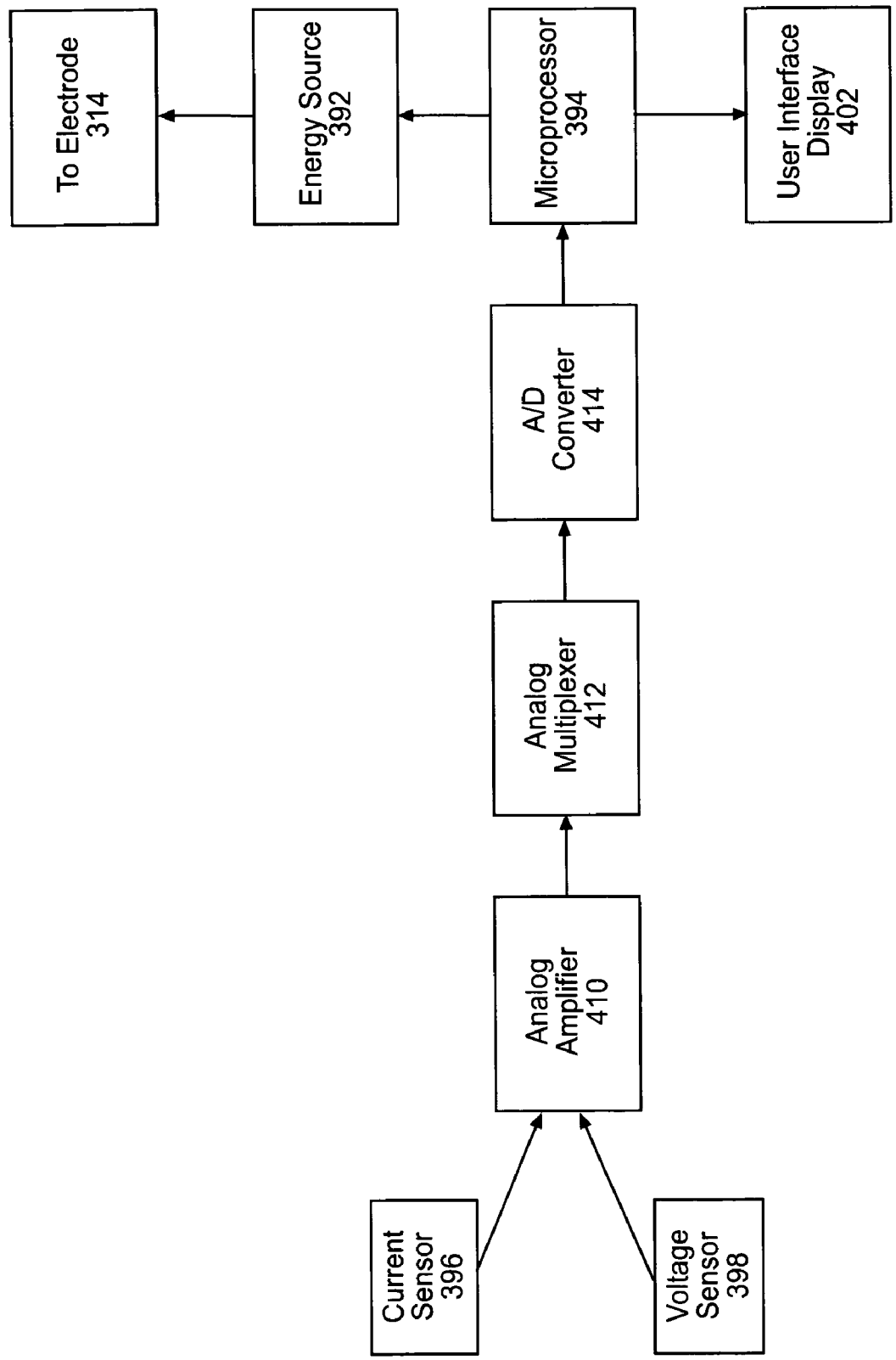
FIG. 30 depicts a block diagram of an analog amplifier, analog multiplexer and microprocessor used with the feedback control system of FIG. 29.

As illustrated in FIG. 30, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394. Microprocessor 394 maybe a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 with power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 31:
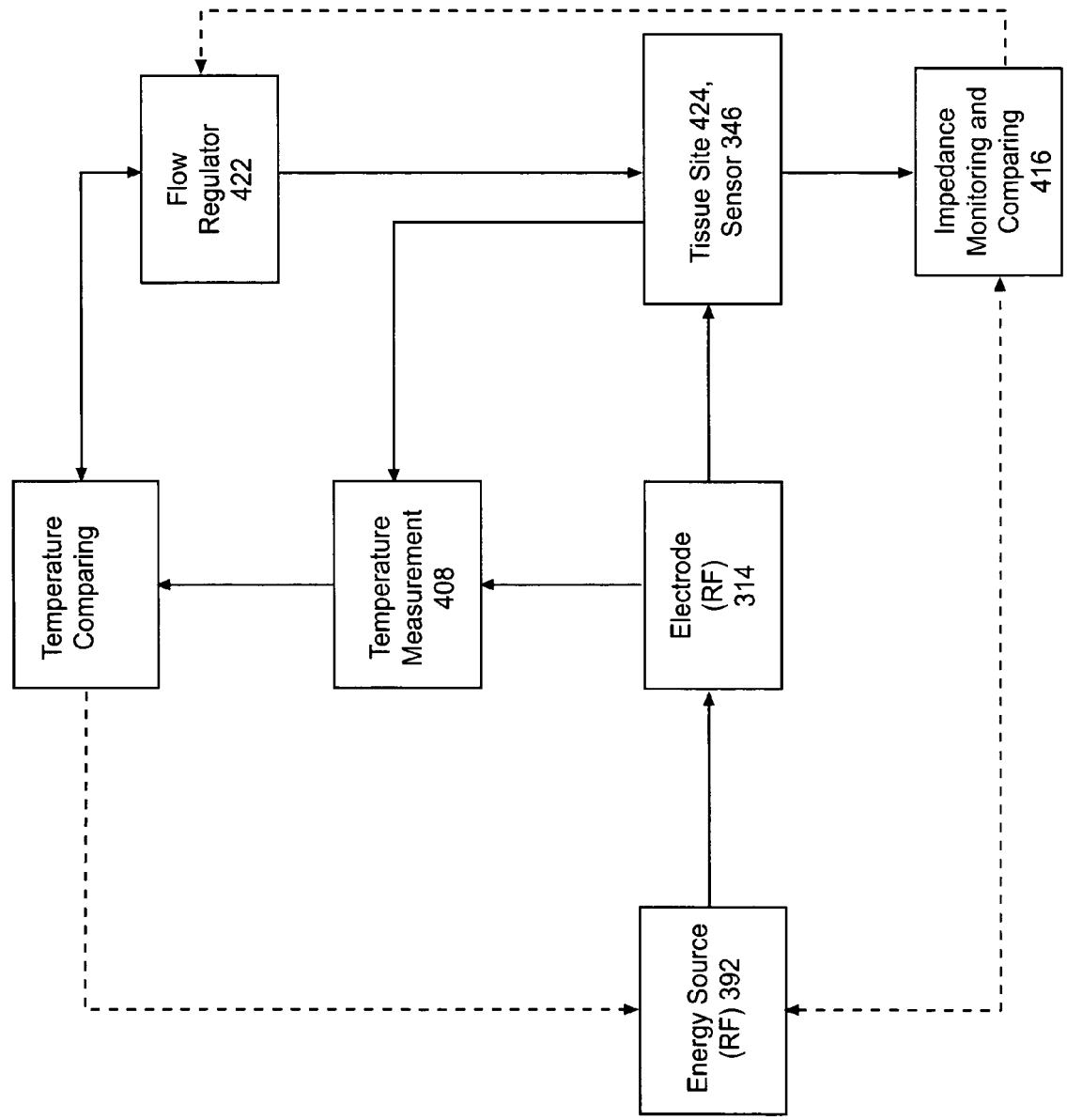
FIG. 31 depicts a block diagram of the operations performed in the feedback control system depicted in FIG. 29.

FIG. 31 illustrates a block diagram of a temperature/impedance feedback system that can be used to control the flow rate and duration of cooling fluid 100 through continuous lumen 102 to expandable and conforming members 16, 26 and 40 and/or RF electrode 314. Energy is delivered to RF electrode 314 by energy source 392, and applied to tissue site 424. A monitor 416 ascertains tissue impedance, based on the energy delivered to tissue, and compares the measured impedance value to a set value. If the measured impedance exceeds the set value, a disabling signal 418 is transmitted to energy source 392, ceasing further delivery of energy to RF electrode 314. If measured impedance is within acceptable limits, energy continues to be applied to the tissue. During the application of energy sensor 346 measures the temperature of tissue and/or RF electrode 314. A comparator 420 receives a signal representative of the measured temperature and compares this value to a pre-set signal representative of the desired temperature. Comparator 420 sends a signal to a flow regulator 422 connected to an electronically controlled micropump (not shown) representing a need for an increased cooling fluid 100 flow rate, if the tissue temperature is too high, or to maintain the flow rate if the temperature has not exceeded the desired temperature.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method of forming a composite lesion pattern in a tissue region at or near a sphincter comprising the steps of:
   providing a catheter having a plurality of energy delivery devices coupled to the catheter,
   introducing the catheter at least partially into the sphincter, and
   delivering energy from the energy delivery devices to produce the composite lesion pattern, the composite lesion pattern comprising a radial distribution of lesions about the tissue region and a longitudinal distribution of lesions along the tissue region.

2. A method as in claim 1 wherein the pattern is a concentric circle of lesions all at a fixed depth along the radial axis of the sphincter.

3. A method as in claim 1 wherein the pattern is a wavy or folded circle of lesions at varying depths along the radial axis of the sphincter.

4. A method as in claim 1 wherein the pattern is a random distribution of lesions at varying depths and evenly spaced in a radial direction.

5. A method as in claim 1 wherein the pattern is an eccentric pattern of lesions in one or more radial locations.

6. A method as in claim 1, further comprising the step of introducing a cooling fluid to cool at least a portion of the tissue region.

7. A method as in claim 1, further comprising the step of introducing a cooling fluid to cool at least a portion of at least one energy delivery device.

* * * * *